(12) United States Patent
Erry et al.

(10) Patent No.: US 8,731,965 B2
(45) Date of Patent: May 20, 2014

(54) COLLABORATIVE MULTI-FACILITY MEDICATION MANAGEMENT SYSTEM

(76) Inventors: Poonam Erry, Fremont, CA (US); Shah Vikram Jung, Fremont, CA (US)

( * ) Notice: Subject to any disclaimer, the term of this patent is extended or adjusted under 35 U.S.C. 154(b) by 316 days.

(21) Appl. No.: 12/838,433

(22) Filed: Jul. 17, 2010

(65) Prior Publication Data

US 2011/0015947 A1 Jan. 20, 2011

Related U.S. Application Data

(60) Provisional application No. 61/226,737, filed on Jul. 19, 2009.

(51) Int. Cl.
*G06Q 50/00* (2012.01)
(52) U.S. Cl.
USPC .................................. 705/3; 705/2
(58) Field of Classification Search
USPC .......................................... 705/2, 3
See application file for complete search history.

(56) References Cited

U.S. PATENT DOCUMENTS

| | | | |
|---|---|---|---|
| 2004/0039628 A1* | 2/2004 | Thompson et al. | 705/9 |
| 2004/0243435 A1* | 12/2004 | Williams | 705/2 |
| 2005/0165623 A1* | 7/2005 | Landi et al. | 705/2 |
| 2006/0036619 A1 | 2/2006 | Fuerst et al. | |
| 2006/0143060 A1* | 6/2006 | Conry et al. | 705/8 |
| 2006/0173712 A1 | 8/2006 | Joubert | |
| 2006/0184524 A1 | 8/2006 | Pollanz | |
| 2007/0055552 A1* | 3/2007 | St. Clair et al. | 705/3 |
| 2007/0168221 A1 | 7/2007 | Blotter et al. | |
| 2008/0059242 A1 | 3/2008 | Stanford | |
| 2010/0169220 A1* | 7/2010 | Choing et al. | 705/51 |
| 2010/0262436 A1* | 10/2010 | Chen et al. | 705/3 |

* cited by examiner

*Primary Examiner* — Mark Holcomb
*Assistant Examiner* — Jonathan K Ng
(74) *Attorney, Agent, or Firm* — Ash Tankha; Lipton Weinberger & Husick

(57) ABSTRACT

A computer implemented method and system is provided for managing health care and obtaining analytical insights using information related to health care in a collaborative environment. Health care users and health care providers access a medication management platform in the collaborative environment. The medication management platform comprises a medication management application and a research repository. The health care users and the health care providers interact and communicate with each other in the collaborative environment using collaborative tools provided on the medication management platform. The medication management application acquires health care information of the health care users' personal health records populated from health care information sources. The medication management application monitors and tracks the acquired health care information. The medication management application updates the de-identified research repository by consolidating the monitored and tracked health care information. The medication management application analyzes the consolidated health care information for obtaining the analytical insights.

26 Claims, 16 Drawing Sheets

PATIENT: JOHN JOHNSON

MEDICAL SHEET SEPTEMBER 2002

| MEDICATION | NOTES | DAY/TIME | 1 | 2 | 3 | 4 | 5 | 6 | 7 | 8 | 9 | 10 | 11 | 12 | 13 | 14 | 15 | 16 | 17 | 18 | 19 | 20 | - | - | 31 |
|---|---|---|---|---|---|---|---|---|---|---|---|---|---|---|---|---|---|---|---|---|---|---|---|---|---|
| PROCARDIA ORAL | 1 TABLET OF 30 MG | 8:00 AM | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | | | |
| | 2 TABLETS OF 30 MG | 12:00 PM | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | | | |
| | 1 TAB OF 30 MG | 6:00 PM | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | ✓ | | | |
| CEPHALEXIN ORAL | 5ML LIQ DROPS | 8:00 AM | ✓ | | | | ✓ | | ✓ | | ✓ | | ✓ | | ✓ | | ✓ | ✓ | ✓ | | ✓ | | | | |
| | 5ML LIQ DROPS | 12:00 PM | ✓ | ✓ | ✓ | | ✓ | | | | ✓ | | ✓ | | ✓ | | ✓ | ✓ | ✓ | | ✓ | | | | |
| | 5ML LIQ DROPS | 6:00 PM | ✓ | ✓ | ✓ | | ✓ | | ✓ | | ✓ | | ✓ | | ✓ | | ✓ | ✓ | ● | | ✓ | | | | |
| | 5ML LIQ DROPS | 9:00 PM | ✓ | | | | | | | | | | | | | | | | | | | | | | |
| MACRODANTIN ORAL | 2 CAPSULES OF 50 MG | 8:00 AM | | ✓ | | | | | | | ✓ | | | | | | ✓ | ✓ | | | | | | | |
| | 1 CAPSULE OF 50 MG | 6:00 PM | | ✓ | | | | | | | ✓ | | | | | | ✓ | ✓ | | | | | | | |
| NITROGLYCERIN TRANSDERMAL PATCH - 5 SQ. CM | APPLY PATCH | 8:00 AM | | | | | | | | ✓ | | | | | | | | | | | | | | | ✓ |
| | REMOVE PATCH | 6:00 PM | | | | | | | | | ✓ | | | | | | | | | | | | | | ✓ |
| TYLENOL | 1 TO 2 GELCAPS 500MG | AS NEEDED | | | | | | | | | | | | | | | | | | | | | | | |
| PULSE | RECORD | 8:00 AM | | ✓ | | | | | | | | | | | | | | ✓ | | | | | | | |
| TEMPERATURE | RECORD | 8:00 AM | | ✓ | | | | | | | ✓ | | | | | | | ✓ | | | | | | | |
| BLOOD PRESSURE | RECORD | 8:00 AM | ✓ | | | | | | | | ✓ | | | | | | | ✓ | | | | | | | |

| DIAGNOSIS: OSTEOPOROSIS AND LUMBAR COMPRESSION | | ALLERGIES: PEANUTS, EGGS | DOB: 04/11/52 AGE: 50 | ADMIT: 03/20/02 |
|---|---|---|---|---|
| PATIENT: JOHN JOHNSON | ROOM 301 – WEST WING | PRIMARY PHYS: DR. JONES (408) 555-1212 SEC. PHYS: DR. EDWARD (408) 555-1212 | PRIMARY PHARMACY: LONGS | |

▼ ▼  AUG/OCT  ▲ ▲    VIEW COMMENTS    PRINT    CLOSE

COLLABORATIVE MULTI-FACILITY MEDICATION MANAGEMENT SYSTEM

CROSS REFERENCE TO RELATED APPLICATIONS

This application claims the benefit of provisional patent application No. 61/226,737 titled "Collaborative Multi Facility Medication Management System", filed on Jul. 19, 2009 in the United States Patent and Trademark Office.

The specification of the above referenced patent application is incorporated herein by reference in its entirety.

BACKGROUND

The computer implemented method and system disclosed herein, in general, relates to health care services. More particularly, the computer implemented method and system disclosed herein relates to managing health care and obtaining analytical insights using information related to health care in a collaborative environment.

In the United States, there are approximately 38,000 assisted living facilities (ALFs) providing housing and supervision, or assistance with activities of daily living (ADLs) to about 975,000 people. The average age of residents in ALFs is 85 years and, on an average, the ALF residents are on six different prescriptions per month.

In ALFs, medication is often administered by unlicensed assistive personnel who operate outside of a nurse-delegation model but are entrusted with great responsibilities including, for example, medication profiling, medication monitoring, identification of drug-drug, drug-food and drug-lab interaction, and manual coordination with a resident's pharmacy, physician and family. This issue is further exacerbated by the fact that there is nearly an 80% turnover rate for these personnel. An estimated 106,000 fatal adverse drug events (ADEs) occur annually in the US. ALF residents tend to suffer from multiple chronic conditions, visit multiple physicians, and obtain medications from multiple pharmacies locally, by mail order, via the internet, etc. This puts them at a higher risk for adverse drug events (ADEs). A January 2008 survey conducted by the Center for Excellence in Assisted Living (CEAL) showed that the most likely types of medication errors include (i) medication out of stock or not delivered to an assisted living facility (ALF) due to dispensing errors, (ii) medication given at the wrong time due to administering errors, (iii) medication given at the wrong dose due to administering errors, and (iv) wrong medication sent by the pharmacy due to dispensing errors.

Apart from the harm of ADEs to residents, assisted living facility (ALF) managers are deeply concerned about the potential liability of managing resident medications. A single medication error can result in over a $150,000 claim, and professional liability insurance can range between about 10% to about 15% of service costs. Hence, there is a need for a system that reduces adverse drug events (ADEs) for residents, improves compliance for staff, and lowers liability costs for ALFs.

Furthermore, assisted living facility (ALF) residents constitute a large cohort of high medication users whose medication usage is managed and logged on a daily basis. Their medication prescription, administration, usage and compliance information can provide invaluable research insights with significant potential benefits to multiple stakeholders including seniors, assisted living industries, pharmaceuticals, physicians, health care payers, government organizations, etc. Therefore, there is a need for a system or an application that facilitates harvesting of ALF medication data for research purposes.

Hence, in view of the foregoing, there is a long felt but unresolved need for a computer implemented method and system that manages health care and obtains analytical insights related to health care in a collaborative environment.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The computer implemented method and system disclosed herein addresses the above stated need for managing health care and obtaining analytical insights related to health care in a collaborative environment. A medication management platform accessible by multiple health care users and health care providers is provided in the collaborative environment. The health care users and the health care providers are, for example, senior citizens, assisted living facilities, assisted living facility (ALF) residents, nursing homes, care giving facilities, pharmaceuticals, physicians, health care payers, government organizations, etc. The medication management platform is, for example, a cloud computing based platform implemented as a service for developing and hosting scalable web applications and services for managing health care information. The medication management platform comprises a medication management application and a research repository component. Multiple collaborative tools are provided on the medication management platform for enabling the health care users and the health care providers to interact and communicate with each other in the collaborative environment. The collaboration tools comprise, for example, hosted applications for electronic mail, chat, instant messaging, calendar, voice and video messaging, online sharing of documents, work optimization elements, etc. The collaboration tools facilitate collaboration between the health care users and the providers, assisted living facility medication managers, assisted living facility residents, resident families, pharmacies, physicians, etc.

The medication management application acquires health care information of the health care users' personal health records populated from multiple health care information sources using, for example, the collaborative tools. Online portable personal health records of the health care users are acquired as one of the health care information sources. These online portable personal health records are integrated with the medication management application for acquiring specific health care information related to the health care users. The medication management application monitors and tracks the acquired health care information. The medication management application updates a de-identified research repository of the research repository component by consolidating the monitored and tracked health care information. The medication management application analyzes the consolidated health care information in the updated research repository for obtaining analytical insights related to health care.

The research repository is, for example, a cloud computing based scalable research repository that incorporates different levels of security, de-identification of the consolidated health care information for safeguarding the privacy of the health care users, and provides scalable access to researchers. The research repository component of the medication management platform further comprises an analytical processor. The analytical processor provides an analytical visualization dashboard for rendering pre-built analytical insights and trends based on the consolidated health care information. The research repository component comprises multiple application programming interfaces (APIs) for querying and extracting data, policies, and metadata to facilitate research using the research repository. The research repository comprises multiple analytical data registries for obtaining the analytical insights that facilitate research on, for example, aging processes, age-related diseases and special needs of aged health care users, drug post-marketing surveillance, early detection of adverse drug events, study of prescription trends and usage, study of compliance of medication by the health care users, identification of off-label drug use, etc.

The medication management application acquires and stores prescription information and user information of the health care users across the health care providers subscribing to the medication management platform. The prescription information and the user information are acquired from the online portable personal health records of each of the health care users. The medication management application generates a daily medication schedule for each of the health care users based on administration instructions of the health care providers for prescription schedules of each of the health care users. The medication management application also generates a facility master schedule for each of the health care providers for managing schedules of health care users and staff members of each of the health care providers. The medication management application also tracks job schedules of each of the staff members of the health care providers and creates daily task lists for each of the staff members by collating information from the job schedules and the facility master schedule.

The medication management application further comprises a schedule optimization engine for evaluating, on a daily basis, availability schedules of the staff members of each of the health care providers against medication administration needs for each day from the facility master schedule for creating daily task lists for managerial planning and optimization. The medication management application further generates daily task lists for the staff members of each of the health care providers based on recommendations from the schedule optimization engine. The medication management application generates reports for operational and regulatory management to ensure health insurance portability and accountability act (HIPAA) compliance and compliance with state regulations, and to facilitate managerial tracking.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

FIG. 3 exemplarily illustrates a sample resident daily medication schedule generated by a medication management application on a medication management platform.

FIG. 4 exemplarily illustrates a sample daily task list generated by the medication management application on the medication management platform.

FIG. 8D exemplarily illustrates a screenshot of a sample resident personal health record integrated with the medication management application on the medication management platform.

FIG. 8H exemplarily illustrates a screenshot of a sample resident registration web page for assisted living administration.

DETAILED DESCRIPTION OF THE INVENTION

Figure 1:
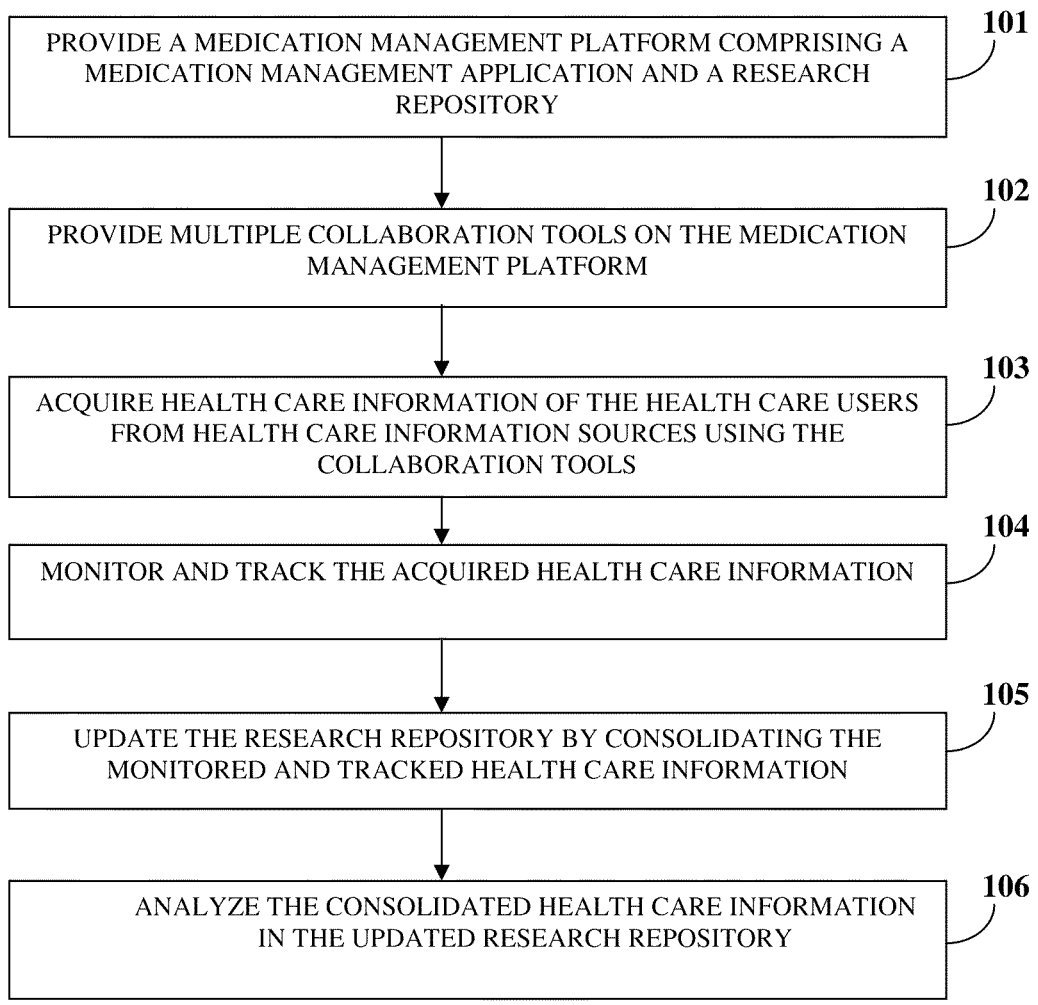
FIG. 1 illustrates a computer implemented method for managing health care and obtaining analytical insights using information related to health care in a collaborative environment.

FIG. 1 illustrates a computer implemented method for managing health care and obtaining analytical insights using information related to health care in a collaborative environment. As used herein, the term "collaborative environment" refers to a cloud computing based networked environment that incorporates a medication management platform for facilitating interaction, communication, and interactive management of health care between different health care users and health care providers. As illustrated in FIG. 1, the medication management platform used to host web applications and services for managing health care and research, is provided 101. The medication management platform comprises a medication management application and a research repository. The medication management platform is accessible by multiple health care users and health care providers in the collaborative environment. The health care users and the health care providers are, for example, senior citizens, assisted living facilities (ALF), ALF residents, nursing homes, pharmaceuticals, physicians, health care payers, government organizations, etc. As used herein, the term "assisted living facility" refers to a congregate care entity that provides a way for health care users who require some assistance and support to retain a relatively independent lifestyle in a residential atmosphere. Assisted living facilities (ALFs) are provided for health care users who need assistance with their activities of daily living, but wish to live as independently as possible. Residents of assisted living facilities (ALFs) do not need the type of skilled care provided at nursing homes. These residents constitute a large cohort of high medication users whose medication usage is managed and logged on a daily basis.

Multiple collaboration tools are provided 102 on the medication management platform. The collaboration tools comprise, for example, hosted applications for electronic mail (email), applications for calendar, applications for instant messaging, chat applications, applications for voice and video messaging, applications for online sharing of documents on the medication management platform, work optimization elements, etc. The collaboration tools enable the health care users and the health care providers to interact and communicate with each other in the collaborative environment. The collaboration tools provided on the medication management platform facilitate interaction and collaboration between the residents of the ALFs, the residents' families, assisted living facility (ALF) medication administrators and managers, pharmacies, physicians, etc. thereby providing seamless continuity of medication administration to residents when the residents visit their families.

The medication management application acquires 103 the health care information of the health care users from multiple health care information sources. One of the health care information sources comprises, for example, online portable personal health records that are integrated with the medication management application for acquiring specific health care information related to the health care users. The health care information comprises, for example, information related to drug medication, allergies and adverse drug reactions, illness and hospitalization, surgeries and other procedures, vaccinations, laboratory test results, etc. In an embodiment, the medication management application acquires the health care information from the health care users using the collaboration tools on the medication management platform. The health care information sourced from the health care users is stored in online portable personal health records or patient health records (PHR) provided to the health care users. As used herein, PHR refers to an internet based set of tools that allows the health care users to access and coordinate their health care information and allow selective access of the health care information to health care providers and others who need the health care information. The PHR collects and tracks the health care information of the health care users. The collected health care information stored in the personal health records (PHR) allows the medication management platform to scale across residents of assisted living facilities (ALFs), families of the residents of the ALFs, pharmacies, physicians, ALFs, etc. The medication management platform employs the residents' portable personal health records (PHR) as the central source of health care information. The medication management platform extracts and inserts data, for example, medication data, into the PHRs based on access provided by the health care users. The ALF management functions deployed on the medication management platform are built around the PHR of the residents. By using an open PHR, for example, the Google PHR of Google Inc., the medication management platform can deploy the medication management application that is secure and portable across residents, ALFs, resident families, pharmacies, physicians, insurers, etc. In an embodiment, the medication management platform incorporates smart medication carts and dispensers for managing medication of the health care users.

The medication management application monitors and tracks 104 the health care information sourced from the health care users, the online portable personal health records, and other health care information sources. The medication management application consolidates the monitored and tracked health care information and updates 105 the research repository on the medication management platform. The medication management application analyzes 106 the consolidated health care information in the updated research repository for obtaining analytical insights related to health care. The analytical insights comprise, for example, prescription trends, medication compliance among the health care users, etc. The health care users use the updated research repository for understanding prescription or medication usage and compliance among seniors, and for understanding aging processes, age related diseases, etc. The medication management platform tracks daily activities, for example, bathing, exercising, eating, etc. of the residents of the assisted living facilities (ALFs) and correlates the tracked activities with the health care information to obtain additional research insights. The health care users' medication prescription, administration, usage and compliance information provide invaluable research insights with potential benefits to multiple stakeholders, for example, seniors, assisted living industry, pharmaceuticals, physicians, health care payers, government, etc.

Figure 2:
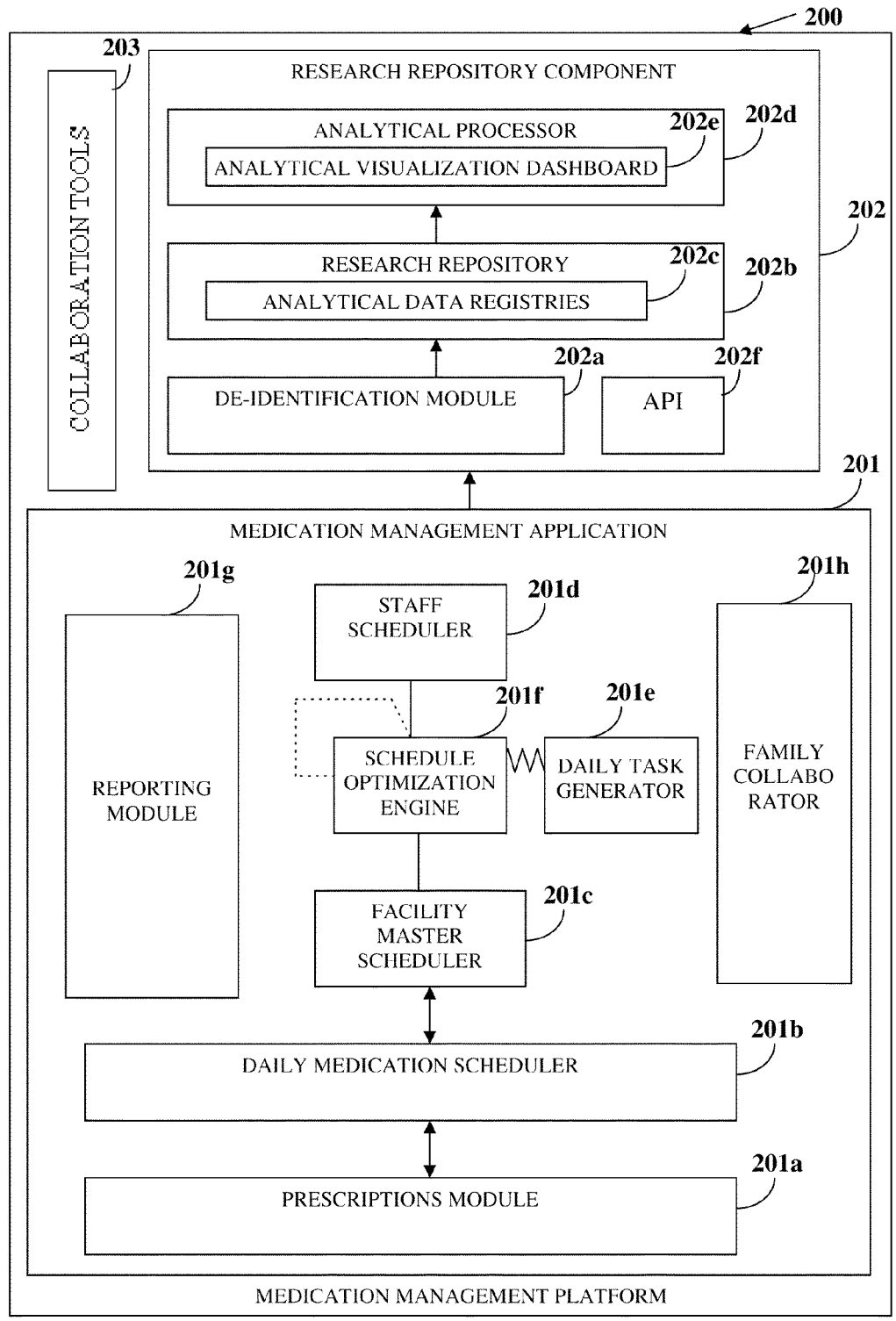
FIG. 2 illustrates a computer implemented system for managing health care and obtaining analytical insights using information related to health care in a collaborative environment.

FIG. 2 illustrates a computer implemented system for managing health care and obtaining analytical insights using information related to health care in a collaborative environment. The computer implemented system disclosed herein obtains analytical insights related to health care information from health care users of, for example, an assisted living facility (ALF). Multiple health care users access the medication management platform 200 in the collaborative environment using collaboration tools 203. The collaboration tools 203 comprise, for example, applications for email, applications for calendar, applications for instant messaging, chat applications, applications for voice and video messaging, applications for online sharing of documents on the medication management platform 200, etc. The collaboration tools 203 acquire health care information of the health care users from the health care information sources and enable the health care users and the health care providers to interact and communicate with each other in the collaborative environment.

The medication management platform 200 comprises a medication management application 201 and a research repository component 202. The medication management application 201 monitors and tracks the acquired health care information. The medication management application 201 comprises a prescriptions module 201a, a daily medication scheduler 201b, a facility master scheduler 201c, a staff scheduler 201d, a schedule optimization engine 201f, a daily task generator 201e, a reporting module 201g, and a family collaborator 201h. The medication management platform 200 combines health care user information from multiple ALFs and creates the research repository component 202 for use to support and accelerate research that improves the health and well being of the health care users.

The prescriptions module 201a implements, for example, the Google™ Health personal health record (PHR) of Google, Inc. with appropriate extensions and linkages. The Google™ Health™ PHR is a web based application. The Google™ Health PHR is based on a subset of the continuity of care record and allows the health care users to build their own health records in a private web space. The Google™ Health PHR comprises the complete and accurate health care information of the health care users. The medication management platform 200 integrates the Google™ Health PHR with the medication management application 201 using the atom publishing protocol (APP). The APP receives the health care information from the health care users, applies coding heuristics, and allows managing heath care profiles of multiple health care users. In an embodiment, the prescriptions module 201a also implements, for example, the Microsoft® HealthVault™ patient health record of Microsoft Corporation.

The prescriptions module 201a acquires and stores prescription information and user information, for example, medication prescription details and resident information, of the health care users herein referred to as "residents", across the health care providers, for example, assisted living facilities (ALFs) subscribing to the medication management platform 200. The prescriptions module 201a acquires the prescription information and the user information from, for example, the online portable personal health records of each of the health care users. The medication management platform 200 restricts access to the medication prescription details and the resident information at the individual resident level. The medication prescription details and the resident information are made available programmatically within the ALF that the resident belongs to. Although the medication management platform 200 restricts access to the medication prescription details and the resident information by other ALFs, the residents within an ALF are allowed to share the medication prescription details and the resident information with family members and other health care providers.

In an embodiment, the medication management platform 200 provides an interface for prescription systems. The interface for prescription systems, in communication with the prescriptions module 201a, facilitates the tracking of prescription shipment and packaging information and correlates shipment and prescription crosscheck.

The daily medication scheduler 201b is based on, for example, the Google Calendar™ application of Google Inc. The Google Calendar™ is a web based application for time management. The daily medication scheduler 201b generates the daily medication schedule for each of the residents of the assisted living facilities (ALFs). The daily medication schedule is based on the administration instructions for the resident's prescriptions. The daily medication scheduler 201b makes the daily medication schedule available to the residents' families. FIG. 3 exemplarily illustrates a platform independent format of a sample resident daily medication schedule generated by the medication management application 201 on the medication management platform 200. The daily medication scheduler 201b sends reminders and alerts for medication administration based on the daily medication schedule.

The facility master scheduler 201c combines the schedules of all the residents of the assisted living facility (ALF) and creates a facility master schedule for the ALF. The facility master schedule is used for generating the actual task lists for managing schedules of the staff members, for example, the medication administrators of the ALF. The staff scheduler 201d tracks the job schedules for medical technicians and other staff members who are responsible for medication administration. The staff scheduler 201d collates the job schedule information with the facility master schedule to create daily task lists for each of the staff members. The daily task lists assist the staff of the ALFs in their daily work.

The schedule optimization engine 201f is an algorithm driven engine. The schedule optimization engine 201f evaluates, on a daily basis, the availability schedules of the staff members, for example, the medical technicians, against the medication administration needs for each day from the facility master schedule and creates daily task lists for each day. The evaluation performed by the schedule optimization engine 201f guides the management of assisted living facilities (ALFs) in planning and optimizing their efforts and in generating daily operating efficiencies. The medication management application 201 applies algorithms to correlate and optimize medical staff schedules with residents' medication schedules to minimize effort and ensure compliance.

Figure 4:
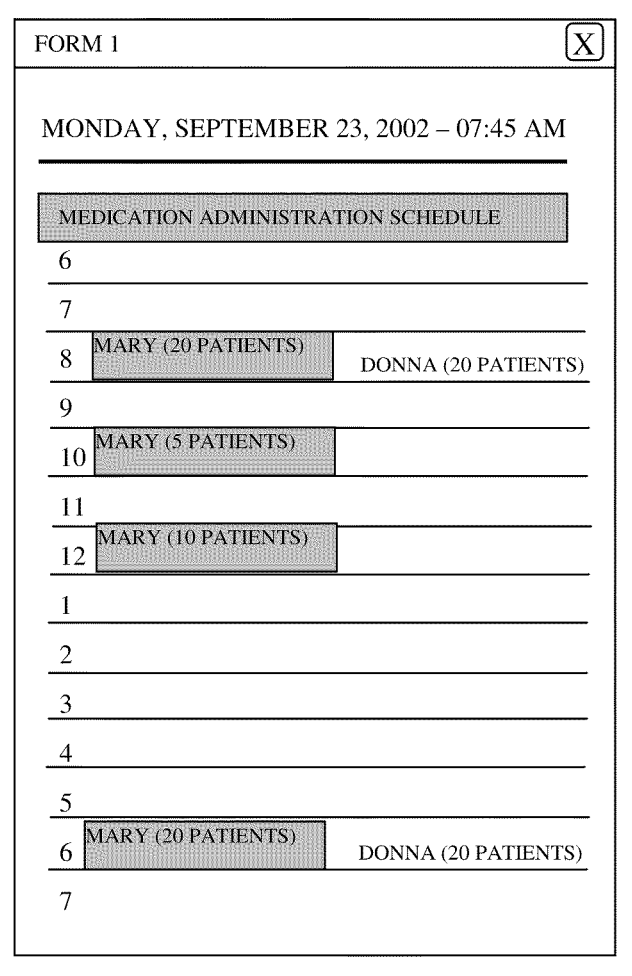

The daily task generator 201e generates daily task lists for the staff members, for example, the medical technicians based on the recommendations from the schedule optimization engine 201f. FIG. 4 exemplarily illustrates a platform independent format of a sample daily task list generated by the medication management application 201 on the medication management platform 200.

The reporting module 201g generates and handles reports for both operational and regulatory management. The information required for the reports is derived from the logging aspects of the medication management platform 200 to ensure compliance with health insurance portability and accountability act (HIPAA), state regulations, and to facilitate other managerial tracking.

The family collaborator 201h tracks information of families of the residents of ALFs and provides a mechanism for the families of the residents to reach out to the ALF medical technicians and vice versa. The family collaborator 201h enables the families of residents to be integrally and actively involved in resident care.

As exemplarily illustrated in FIG. 2, the research repository component 202 comprises a de-identification module 202a, an analytical processor 202d, and a research repository 202b. The research repository 202b consolidates the health care information monitored and tracked by the medication management application 201. The analytical processor 202d analyzes the consolidated health care information in the research repository 202b for obtaining analytical insights related to health care. The analytical processor 202d provides an analytical visualization dashboard 202e for rendering prebuilt analytical insights and trends based on the consolidated health care information. The research repository component 202 further comprises application programming interfaces (APIs) 202f, for example, research data APIs 507 exemplarily illustrated in FIG. 5 for querying and extracting data, policies, and metadata to facilitate research using the research repository 202b. The APIs 202f are interfaces defining the ways by which an application program requests for services from an operating system of the medication management platform 200.

The de-identification module 202a de-identifies health care user information for a particular health care provider. For example, the de-identification module 202a de-identifies the resident information for an assisted living facility (ALF). As used herein, the term "de-identification" refers to a process of removal of specific information, for example, name, social security number, medical numbers from the health care information of the health care users to protect the personal identification details of the health care users. The de-identification module 202a meets the privacy requirements of the residents. The de-identified information is stored in the research repository 202b. The de-identified research repository 202b supports research on human aging, studies on prescription trends, medication usage, compliance among seniors, etc. The research repository 202b comprises multiple analytical data registries 202c for obtaining the analytical insights that facilitate research on aging processes, age-related diseases and special needs of aged health care users, drug post-marketing surveillance, early detection of adverse drug events, study of prescription trends and usage, study of compliance of medication by the health care users, identification of off-label drug use, etc.

The analytical visualization dashboard 202e provided by the analytical processor 202d comprises a set of analytical trend information. The analytical trend information is built on the de-identified information provided by the de-identification module 202a in different visualizations. The analytical trend information provides pre-understood insights, for example, trends in usage of a particular medication over time, etc. The analytical visualization dashboard 202e having access to the de-identified information serves as a front-end for analytical queries. The research repository 202b comprising the de-identified information facilitates comparison of prescriptions across health care users correlated with age, sex, and activities of daily living support needed by a health care user.

Figure 5:
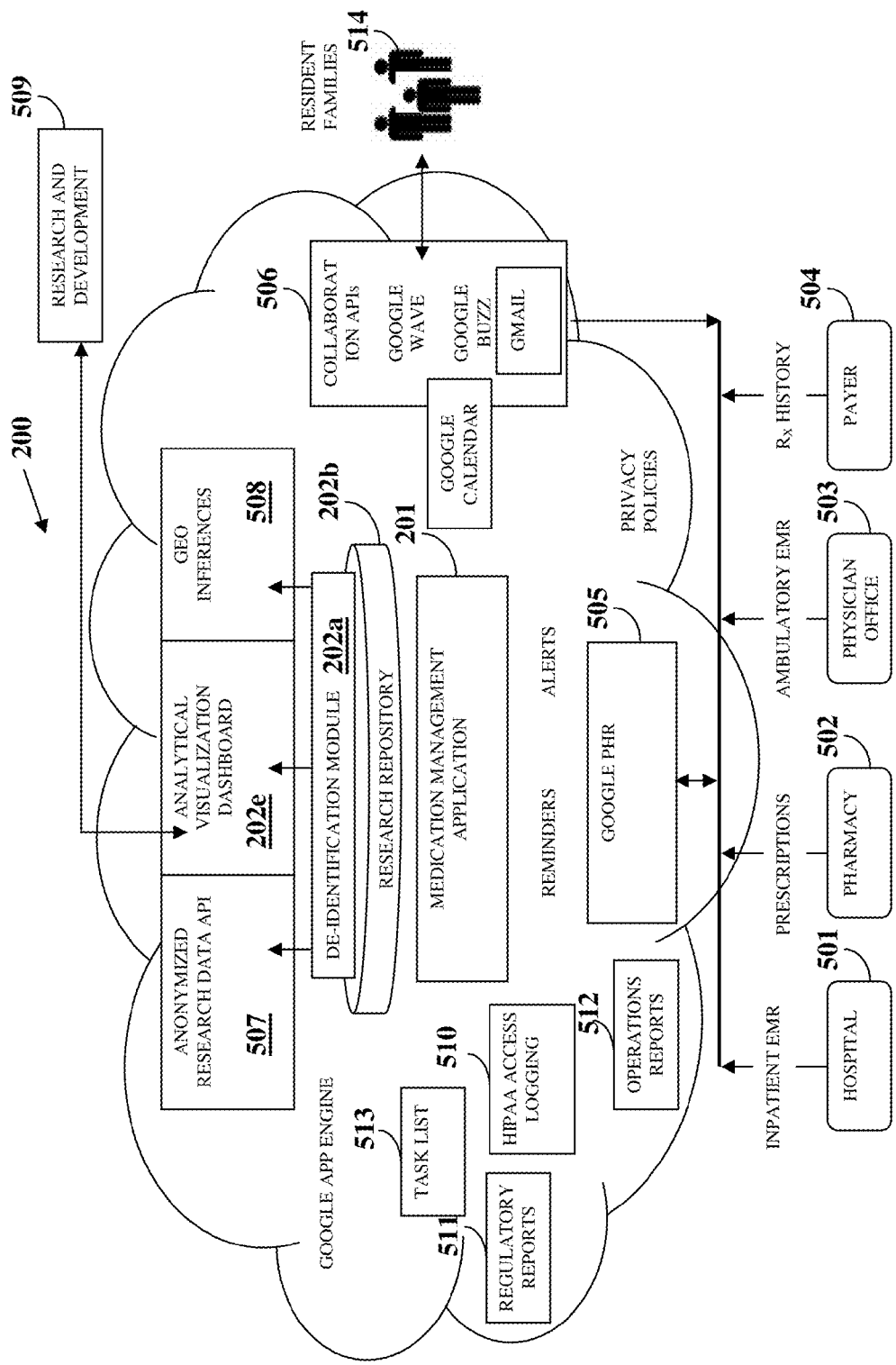
FIG. 5 exemplarily illustrates a cloud computing architecture of the medication management platform.

FIG. 5 exemplarily illustrates a cloud computing architecture of the medication management platform 200. As used herein, the term "cloud computing" refers to a software as a service (SAAS) model in which businesses rent access to applications and information technology (IT) infrastructure that reside on the internet, pay for them on a subscription or per-use basis and provide health care users and health care providers with access to information from anywhere at any time with nothing more than a connected device. The medication management platform 200 is a cloud computing based platform implemented as a service for developing and hosting scalable web applications and services for managing the health care information. The medication management platform 200 is developed using, for example, the Google App engine cloud infrastructure of Google Inc. The Google App engine provides a cost effective web based software development and data management tool for the assisted living facilities (ALFs) and is scalable as adoption grows. The medication management platform 200 leverages other evolving services and tools, for example, Google's services to build a new generation web solution for managing health care.

The medication management platform 200 as exemplarily illustrated in FIG. 5, streamlines the medication administration process for assisted living facilities (ALFs) cost effectively and provides advanced collaboration through the collaboration tools 203, for example, email applications, chat applications, instant messaging applications, and other work optimization elements. In an example, the medication management platform 200 is built on the Google App Engine™ of Google Inc. for providing a scalable, fault-tolerant web application environment. The medication management platform 200 runs applications on Google's massively parallel web infrastructure, which provides a robust development environment coupled with a fully maintained and supported infrastructure at minimal cost. In another embodiment, the medication management platform 200 provides an interface to statistical modeling tools, for example, SAS® of SAS Institute Inc., MATLAB® of MathWorks Inc., LabVIEW™ of National Instruments, etc.

The Google App Engine™ comprises language specific frameworks for Python™ and Java™ languages for rapid application development. The Google App Engine™ software development kit (SDK) allows for building applications locally and then deploying to the Google App Engine™ platform. The Google App Engine™ comprises several APIs for leveraging Google™ functionality. The APIs 202f comprise, for example, APIs for working with user accounts, mail APIs for working with mail items, chat APIs for working with voice and video chat, APIs for working with a data store, etc.

The PHR 505, for example, the Google PHR 505 of Google Inc. allows the health care users to access and coordinate their lifelong health information and make appropriate parts of their health care information available to those who need the health care information. Multiple electronic and paper-based information sources for each of the health care users, for example, the inpatient electronic medical record implemented by one or more hospitals 501, prescriptions from pharmacies 502, ambulatory EMR from physician offices 503, and medical ($R_x$) history from health care payers 504 are collected in the Google PHR 505. The medication management platform 200 integrates the PHR 505 with the multi-entity medication management application 201 and the two in conjunction feed the research repository 202b. The research repository 202b is a cloud computing based scalable research repository incorporating different levels of security, de-identification of the consolidated health care information for safeguarding privacy of the health care users, and scalable access for researchers. The health care information fed into the research repository 202b is de-identified to protect the identity of the health care users. The cloud computing based research repository 202b comprising the de-identified information is massively scalable and accessible with appropriate level of security and provides easy access for researchers. The research repository component 202 comprises APIs 202f, for example, standard research data APIs 507 for data extraction and policies and metadata to facilitate use. The research data APIs 507 of the research repository component 202 allow researchers to query and extract information for research from the research repository 202b. Basic insights and trends are pre-built in the analytical visualization dashboard 202e of the analytical processor 202d. The trends comprise, for example, medication prescription trends, trends in the usage of a particular medication over time, etc. The insights and trends are also correlated with the geography of the health care users to derive geo inferences 508 for research and development 509.

The medication management platform 200 utilizes, for example, Google™ BigTable of Google, Inc. as a data store for the research repository 202b. The research repository 202b of the medication management platform 200 is based on, for example, Google™ BigTable and is integrated with the medication management application 201. Google BigTable is a distributed database system for information storage. The Google BigTable is designed to scale to a very large size and easily accommodates the research repository requirements. The research repository component 202 develops visualization and computationally intensive methods for mining large, non-homogeneous, multi-dimensional datasets to discover knowledge or obtain analytical insights from the acquired health care information. The medication management platform 200 supports rapid information fetching through, for example, Google™ query language (GQL) and data visualization APIs. GQL is a language used to retrieve information from an application engine scalable information store, for example, the Google App Engine's data store.

The cloud computing based research repository 202b comprises state-of-the-art registries, for example, the analytical data registries 202c, used for accelerating research on, for example, aging processes, compliance of medication by seniors, age-related diseases, special needs of aged persons, and for understanding prescription use and trends, etc. The research repository 202b comprises enhanced information on actual drug ingestion for example, smoking status, body mass index, etc.

Pharmaceutical companies use the information in the research repository 202b to conduct drug post marketing surveillance for improving early detection of drugs released in the market that cause unforeseen, unwanted and harmful adverse drug effects (ADEs). The medication management platform 200 implements statistical techniques, for example, cluster analysis, link analysis, deviation detection and disproportionality assessment, etc. for identifying ADEs. The research repository 202b helps in identification of off-label drug use. Physicians and caregivers may use the research repository 202b for formulating evidence based best practices for care.

The medication management platform 200 provides the ability to observe and predict disease outbreaks by analyzing recent prescriptions for tracking infectious disease trends. The medication management platform 200 facilitates collaboration between multiple health care users and providers, for example, medication administrators, residents of assisted living facilities (ALFs), families 514 of residents of the ALFs, pharmacies, physicians, etc. The medication management platform 200 keeps the families 514 of the residents of the ALFs engaged and collaborates with them to ensure satisfaction of the residents and their families 514. The medication management platform 200 also improves communications and facilitates collaboration between the health care providers, for example, between pharmacies and physicians, between medication administrators and residents' families 514, between medication administrators and pharmacies, between medication administrators and physicians, etc. The collaboration on the medication management platform 200 provides direct visibility to physicians and pharmacies into the administration of medication to residents of ALFs. The direct visibility allows appropriate clinical drug interventions and reduces the number of inappropriate and unnecessary medications, thereby reducing medication errors. The medication management platform 200 aids in improving ALF staff productivity, streamlining operations, and enhancing regulatory compliance.

The medication management platform 200 minimizes gaps in the health care information and improves the quality and relevance of the health care information for research purposes. The continuity and improved flow of information created by the collaboration APIs 506, for example, Google Wave, Google buzz, Gmail, etc. of the medication management platform 200 implies more collaboration between all the health care users and the health care providers in different settings resulting in better outcomes for the health care users. The medication management platform 200 also incorporates time management based web applications, for example, the Google calendar, for sending reminders and alerts to the health care users and the health care providers on different schedules of health care management. Moreover, as disclosed in the detailed description of FIG. 2, the staff scheduler 201d creates daily task lists 513 for each of the staff members of the health care providers. Furthermore, the reporting module 201g generates reports, for example, operations reports 512 and regulatory reports 511 for operational and regulatory management. The medication management platform 200 also implements access logging 510 for HIPAA compliance by monitoring and recording accesses to the medication management platform 200 by the health care users, the health care providers, the researchers, etc.

Figure 6:
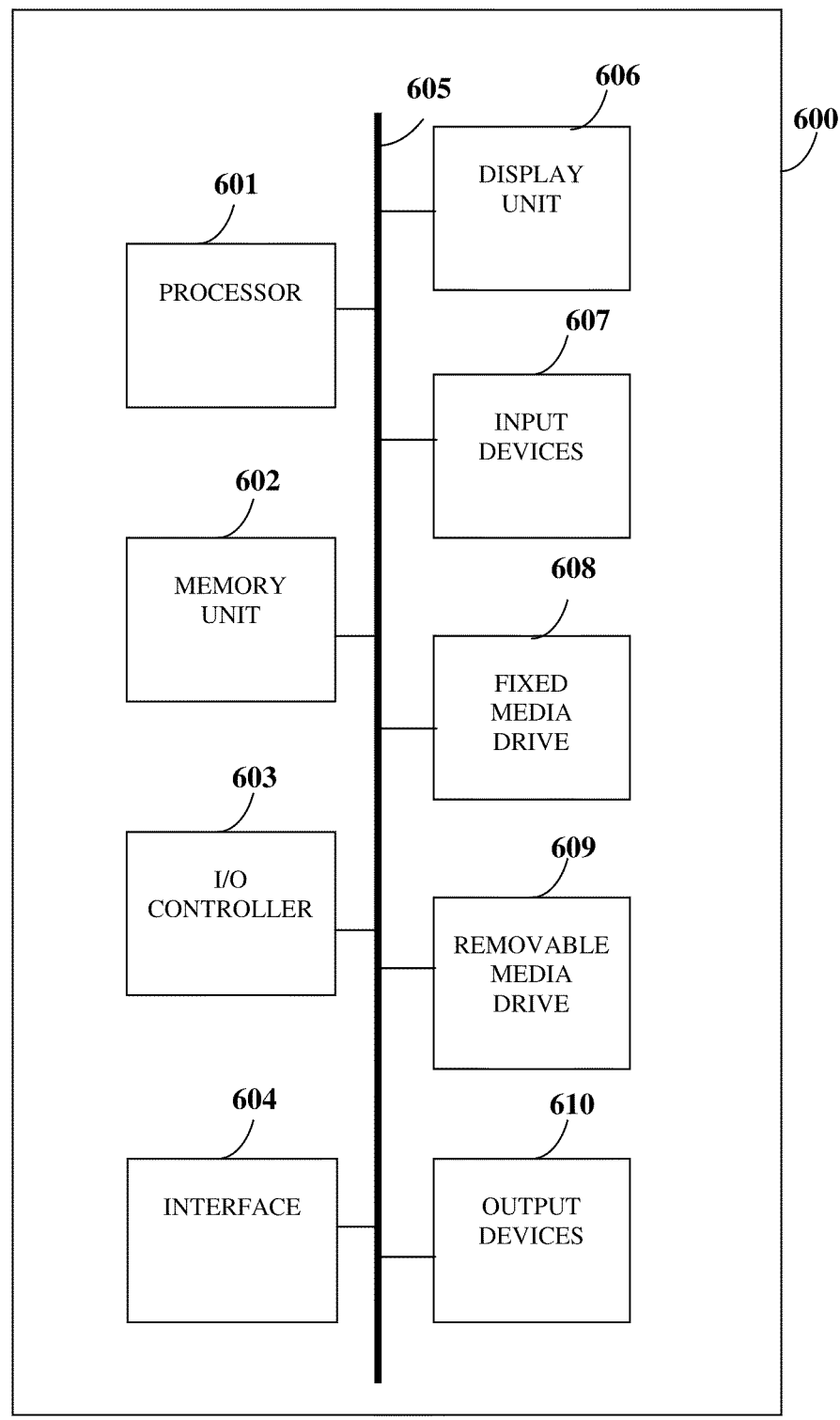
FIG. 6 exemplarily illustrates the architecture of a computer system for managing health care and obtaining analytical insights using information related to health care in a collaborative environment.

FIG. 6 exemplarily illustrates the architecture of a computer system 600 for managing health care and obtaining analytical insights using information related to health care in a collaborative environment. The computer system 600 comprises a processor 601, a memory unit 602 for storing programs and data, an input/output (I/O) controller 603, and a display unit 606 communicating via a data bus 605. The memory unit 602 comprises a random access memory (RAM) and a read only memory (ROM). The computer system 600 further comprises one or more input devices 607, for example, a keyboard such as an alphanumeric keyboard, a mouse, a joystick, etc. The input/output (I/O) controller 603 controls the input and output actions performed by the health care users, the health care providers, the researchers, etc. The computer system 600 communicates with other computer systems through an interface 604, comprising, for example, a Bluetooth™ interface, an infrared (IR) interface, a WiFi interface, a universal serial bus interface (USB), a local area network (LAN) or wide area network (WAN) interface, etc. The computer system 600 is, for example, a server, a data center, or a desktop computer according to the usage and the location of the computer system 600.

The processor 601 is an electronic circuit that can execute computer programs. The memory unit 602 is used for storing programs, applications, and data. For example, the medication management application 201 and the research repository component 202 of the medication management platform 200 are stored on the memory unit 602 of the computer system 600. The memory unit 602 is, for example, a random access memory (RAM) or another type of dynamic storage device that stores information and instructions for execution by the processor 601. The memory unit 602 also stores temporary variables and other intermediate information used during execution of the instructions by the processor 601. The computer system 600 further comprises a read only memory (ROM) or another type of static storage device that stores static information and instructions for the processor 601. The data bus 605 permits communication between the modules, for example, 201a, 201b, 201c, 201d, 201e, 201f, 201g, 201h, 202a, 202b, 202c, 202d, 202e, and 202f of the computer implemented system disclosed herein.

Computer applications and programs are used for operating the computer system 600. The programs are loaded onto the fixed media drive 608 and into the memory unit 602 of the computer system 600 via the removable media drive 609. In an embodiment, the computer applications and programs may be loaded directly through a network. Computer applications and programs are executed by double clicking a related icon displayed on the display unit 606 using one of the input devices 607. The health care users, the health care providers, the researchers, etc. interact with the computer system 600 using a graphical user interface (GUI) of the display unit 606.

The computer system 600 employs an operating system for performing multiple tasks. The operating system manages execution of, for example, the medication management application 201 and the research repository component 202 provided on the computer system 600. The operating system further manages security of the computer system 600, peripheral devices connected to the computer system 600, and network connections. The operating system employed on the computer system 600 recognizes keyboard inputs of the health care users, the health care providers, the researchers, etc., output display, files and directories stored locally on the fixed media drive 608, for example, a hard drive. Different programs, for example, a web browser, an email application, etc., initiated by the user are executed by the operating system with the help of the processor 601, for example, a central processing unit (CPU). The operating system monitors the use of the processor 601.

The medication management application 201 and the research repository component 202 are installed in the computer system 600 and the instructions are stored in the memory unit 602. The health care information is consolidated in the research repository component 202 installed in the computer system 600 of the medication management platform 200 via the interface 604 or a network. A user, for example, a health care provider, initiates the execution of the medication management application 201 and the research repository component 202 by double clicking the icons for the medication management application 201 and the research repository component 202 respectively on the display unit 606. The execution of the medication management application 201 and the research repository component 202 may also be automatically initiated on deploying the medication management application 201 and the research repository component 202 on the medication management platform 200. Instructions for managing health care and obtaining analytical insights using information related to health care are retrieved by the processor 601 from the program memory in the form of signals. The locations of the instructions in the modules, for example, 201a, 201b, 201c, 201d, 201e, 201f, 201g, 201h, 202a, 202b, and 202d are determined by a program counter (PC). The program counter stores a number that identifies the current position in the programs of the medication management application 201 and the research repository component 202.

The instructions fetched by the processor 601 from the program memory after being processed are decoded. The instructions are placed in an instruction register (IR) in the processor 601. After processing and decoding, the processor 601 executes the instructions. For example, the prescriptions module 201a of the medication management application 201 defines instructions for acquiring and storing prescription information and user information of the health care users. The daily medication scheduler 201b defines instructions for generating a daily medication schedule for each of the health care users based on administration instructions of the health care providers. The facility master scheduler 201c defines instructions for generating a facility master schedule for each of the health care providers. The staff scheduler 201d defines instructions for tracking job schedules of each of the staff members of the health care providers and for creating daily task lists for each of the staff members. The schedule optimization engine 201f defines instructions for evaluating, on a daily basis, availability schedules of the staff members of each of the health care providers against medication administration needs. The daily task generator 201e defines instructions for generating daily task lists for the staff members of each of the health care providers based on recommendations from the schedule optimization engine 201f. The reporting module 201g defines instructions for generating reports for operational and regulatory management. The de-identification module 202a defines instructions for de-identifying health care user information for a particular health care provider. The analytical processor 202d of the research repository component 202 defines instructions for analyzing consolidated health care information in the research repository 202b for obtaining analytical insights related to health care, etc. The defined instructions are stored in the program memory or received from a remote server.

The processor 601 retrieves the instructions defined by the prescriptions module 201a, the daily medication scheduler 201b, the facility master scheduler 201c, the staff scheduler 201d, the schedule optimization engine 201f, the daily task generator 201e, the reporting module 201g, the de-identification module 202a, the analytical processor 202d, etc. and executes the instructions.

At the time of execution, the instructions stored in the instruction register are examined to determine the operations to be performed. The specified operation is then performed by the processor 601. The operations include arithmetic and logic operations. The operating system performs multiple routines for performing a number of tasks required to assign the input devices 607, output devices 610, and memory for execution of the medication management application 201 and the research repository component 202. The tasks performed by the operating system comprise assigning memory to the medication management application 201, the research repository component 202 and data, moving data between the memory unit 602 and disk units and handling input/output operations. The operating system performs the tasks on request by the operations and after performing the tasks, the operating system transfers the execution control back to the processor 601. The processor 601 continues the execution to obtain one or more outputs. The outputs of the execution of the medication management application 201 and the research repository component 202 are displayed to the health care user, the health care provider, the researcher, etc. on the display unit 606.

Figure 7:
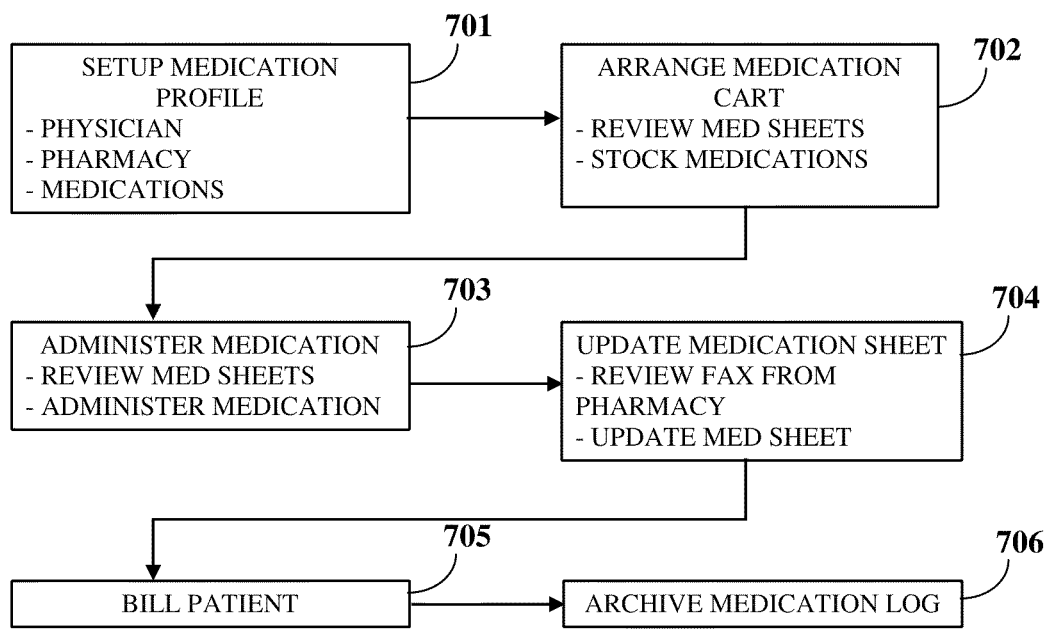
FIG. 7 exemplarily illustrates a workflow diagram for managing health care in an assisted living facility.

Consider an example for managing health care in an assisted living facility (ALF). FIG. 7 exemplarily illustrates a workflow diagram for managing health care in the assisted living facility (ALF). For every ALF resident, a medication profile is established or set up 701 using the medication management application 201. The medication profile comprises information about the physician, pharmacy, and medications. The medication administration records, treatment administration records, nursing aide forms and billing statements all flow from the medication profile. The medication management application 201 acquires the health care information from the medication profile and updates the research repository 202b. A medication cart is arranged 702 by reviewing medication sheets and stocking up the medications. A health care provider reviews the medication sheets to administer 703 the medication to the ALF resident as required. The medication sheets are updated 704 as required after reviewing a facsimile (fax) provided from the pharmacy. The resident patient is billed 705 and the medication log is archived 706 in the research repository 202b.

The medication management platform 200 ensures security and protection of the health care information, for example, patient data, for managing the health care information and restricting access to the subscribing health care users and the health care providers. The medication management platform 200 restricts data access as appropriate and utilizes access control mechanisms depending on the role of the health care user or the health care provider. For example, the medication management platform 200 uses Google Inc.'s implementation of the OAuth protocol to authorize requests to the medication management application 201 and other web applications for accessing the health care information of the health care users. The implementation of the OAuth protocol is based on tokens for accessing the health care information on the medication management platform 200. For example, if the research repository 202b on the medication management platform 200 receives an unauthorized request token from a third party user via Google's authorization server, the authorization server queries the health care user to grant the third party user access to the required health care information on the research repository 202b. If the research repository 202b on the medication management platform 200 receives an authorized request token via the authorization server, the authorized request token is exchanged for an access token. The access token can be used to request data from the research repository 202b through Google's service access servers.

Figure 8A:
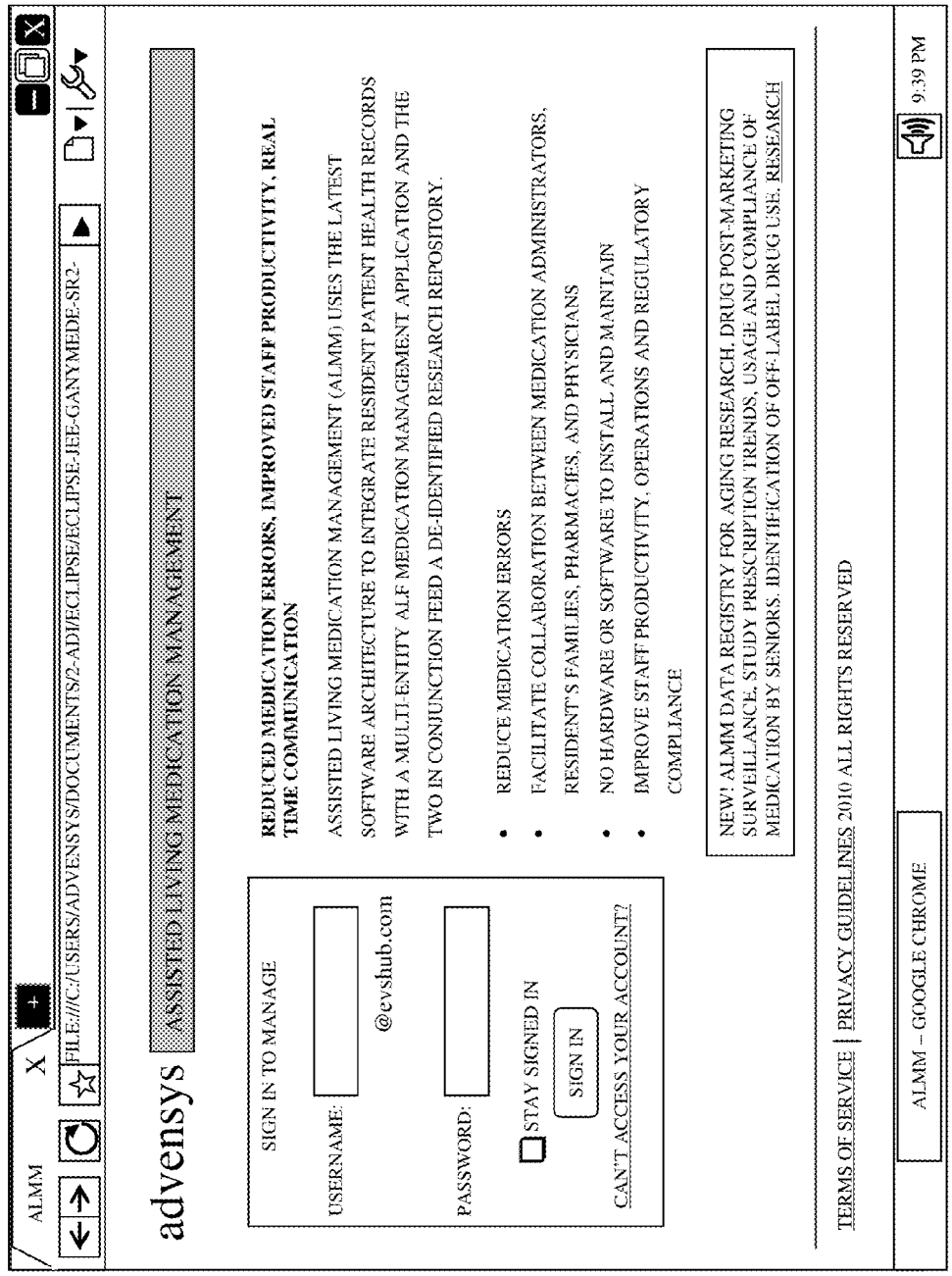
FIG. 8A exemplarily illustrates a screenshot of a login web page for an assisted living facility (ALF) administrator and caregiver for managing health care on the medication management platform.
Figure 8B:
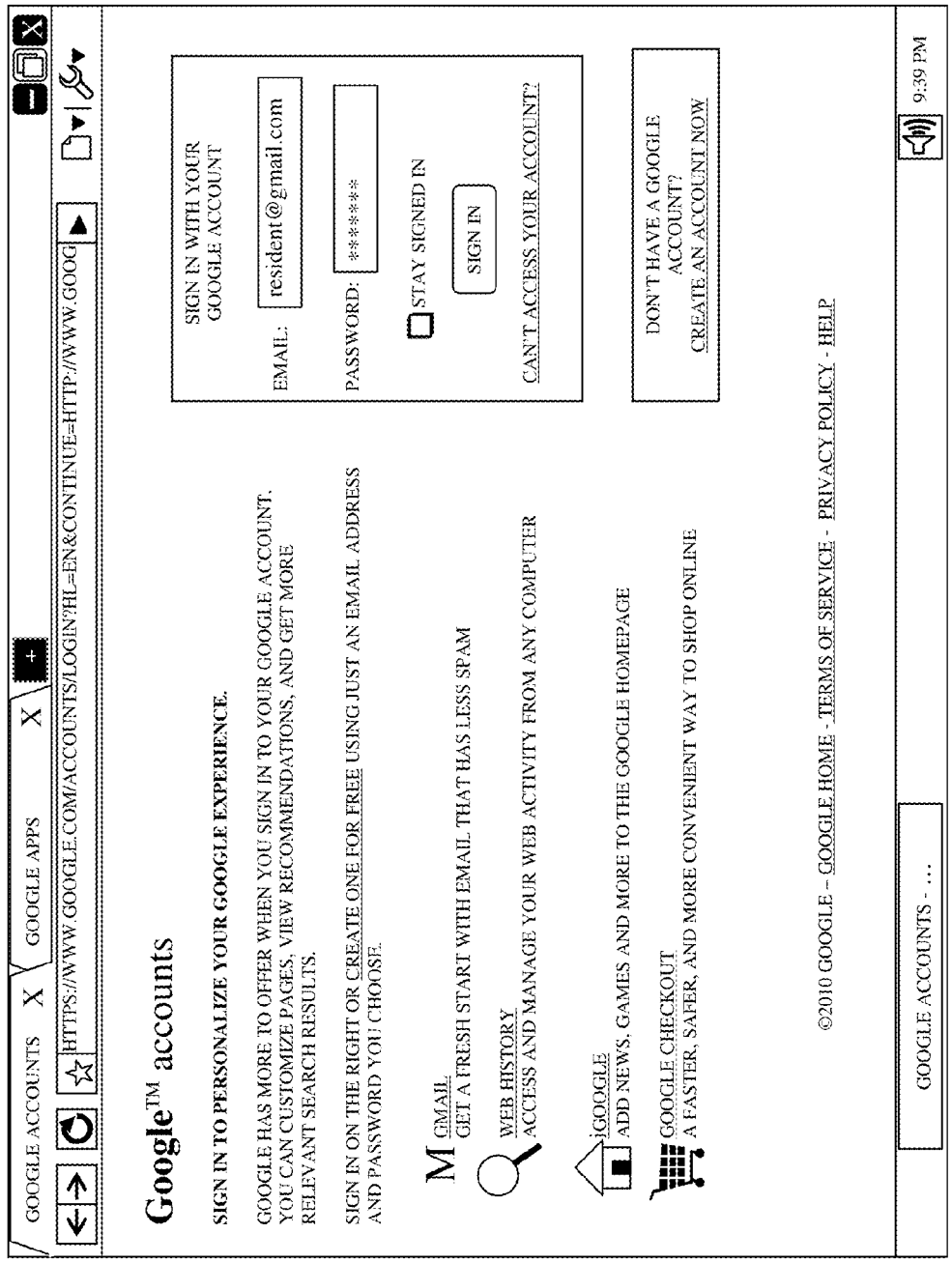
FIG. 8B exemplarily illustrates a screenshot of a login web page for an assisted living facility (ALF) resident for managing health care on the medication management platform.
Figure 8C:
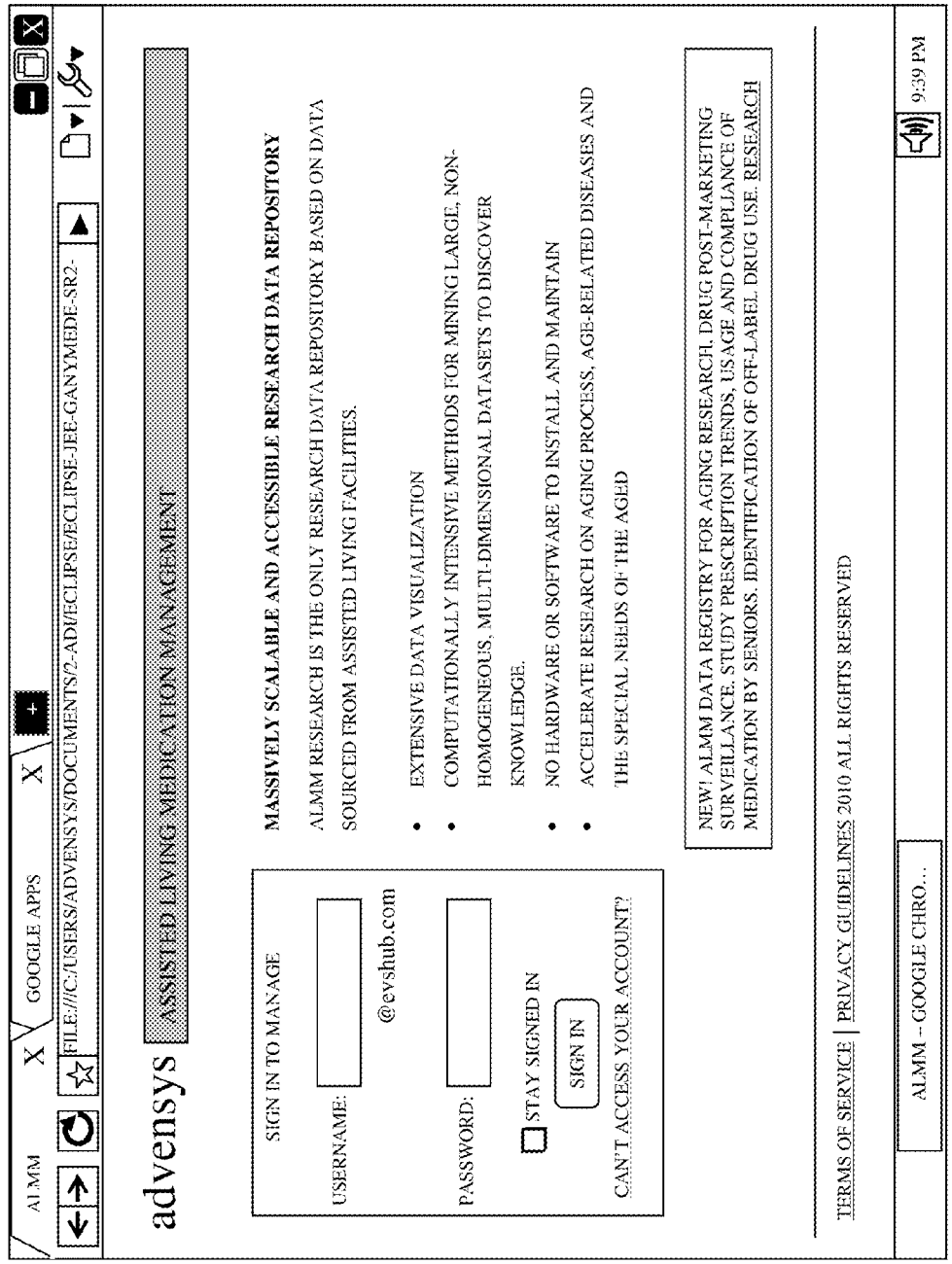
FIG. 8C exemplarily illustrates a screenshot of a login web page for a researcher to obtain analytical insights using information related to health care from a de-identified research repository.

The medication management platform 200 allows assisted living facility (ALF) administrators and caregivers to login to their company domain built on, for example, Google Apps. This enables them to collaborate on administrative tasks with one another and retain the data specific to the ALF within its domain. FIG. 8A exemplarily illustrates a screenshot of a login web page for an assisted living facility (ALF) administrator and caregiver for managing health care on the medication management platform 200. Similarly, the residents login to their individual Google accounts to enter and track their medications and schedules and to interact with their ALF staff through their accounts. FIG. 8B exemplarily illustrates a screenshot of a login web page for an assisted living facility (ALF) resident for managing health care on the medication management platform 200. The medication management platform 200 also allows scientists and researchers to login to the de-identified research repository 202b through Google authenticated accounts on the medication management platform's 200 research specific domains. FIG. 8C exemplarily illustrates a screenshot of a login web page for a researcher to obtain analytical insights using information related to health care from the de-identified research repository 202b.

Figure 8D:
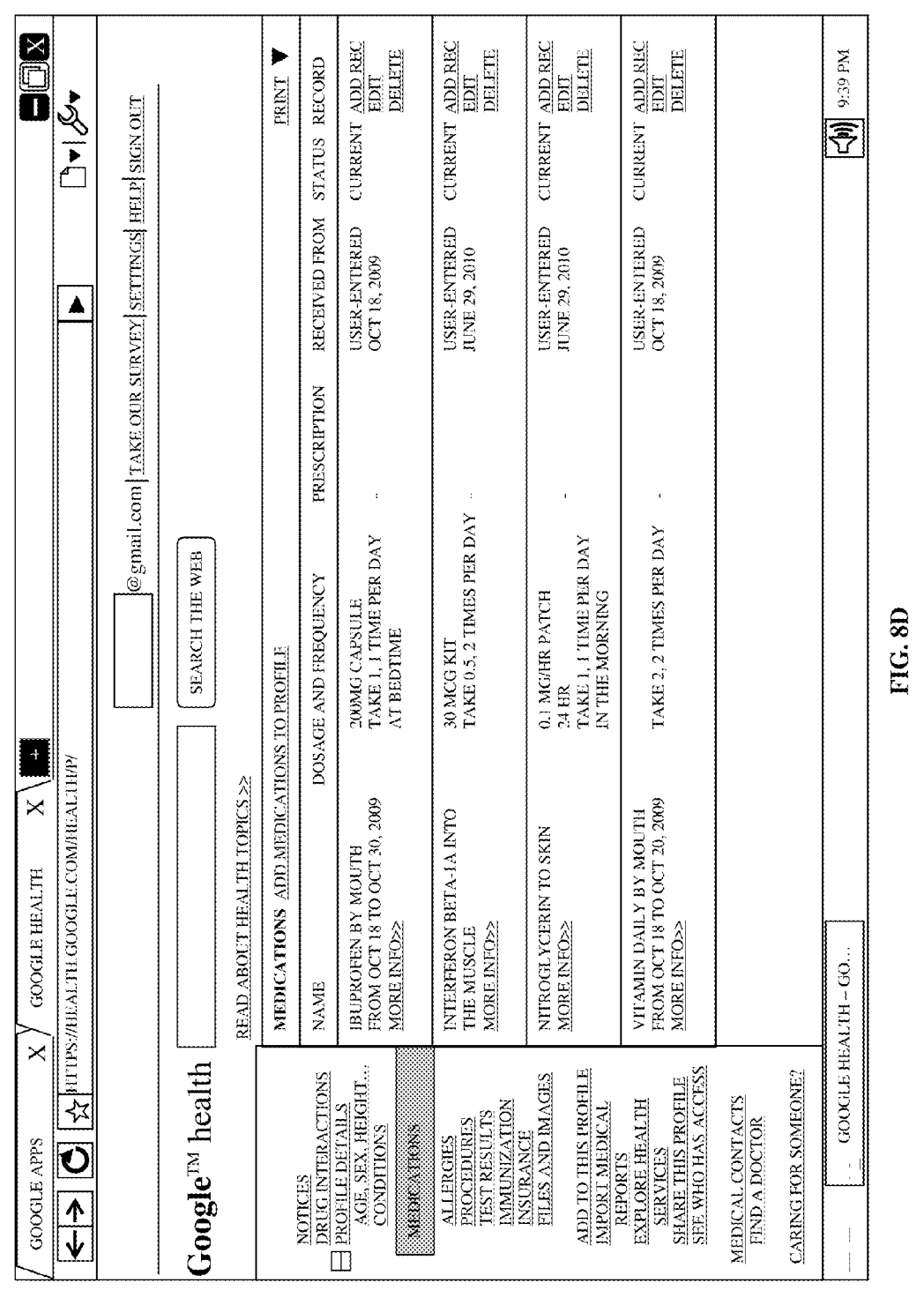

The medication management platform 200 uses open personal health records (PHR) from Google Inc. to deploy the medication management application 201 that is secure and portable across residents, assisted living facilities (ALFs), resident families, pharmacies, physicians, insurers, etc. Individual PHRs feed the prescriptions module 201a. The prescriptions module 201a holds the prescription and resident information for all the residents across all the ALFs subscribing to the medication management platform 200. The medication management platform 200 restricts access to the individual and consolidated health care information. FIG. 8D exemplarily illustrates a screenshot of a sample resident personal health record (PHR) based on Google's health information centralization service integrated with the medication management application 201 on the medication management platform 200.

Figure 8E:
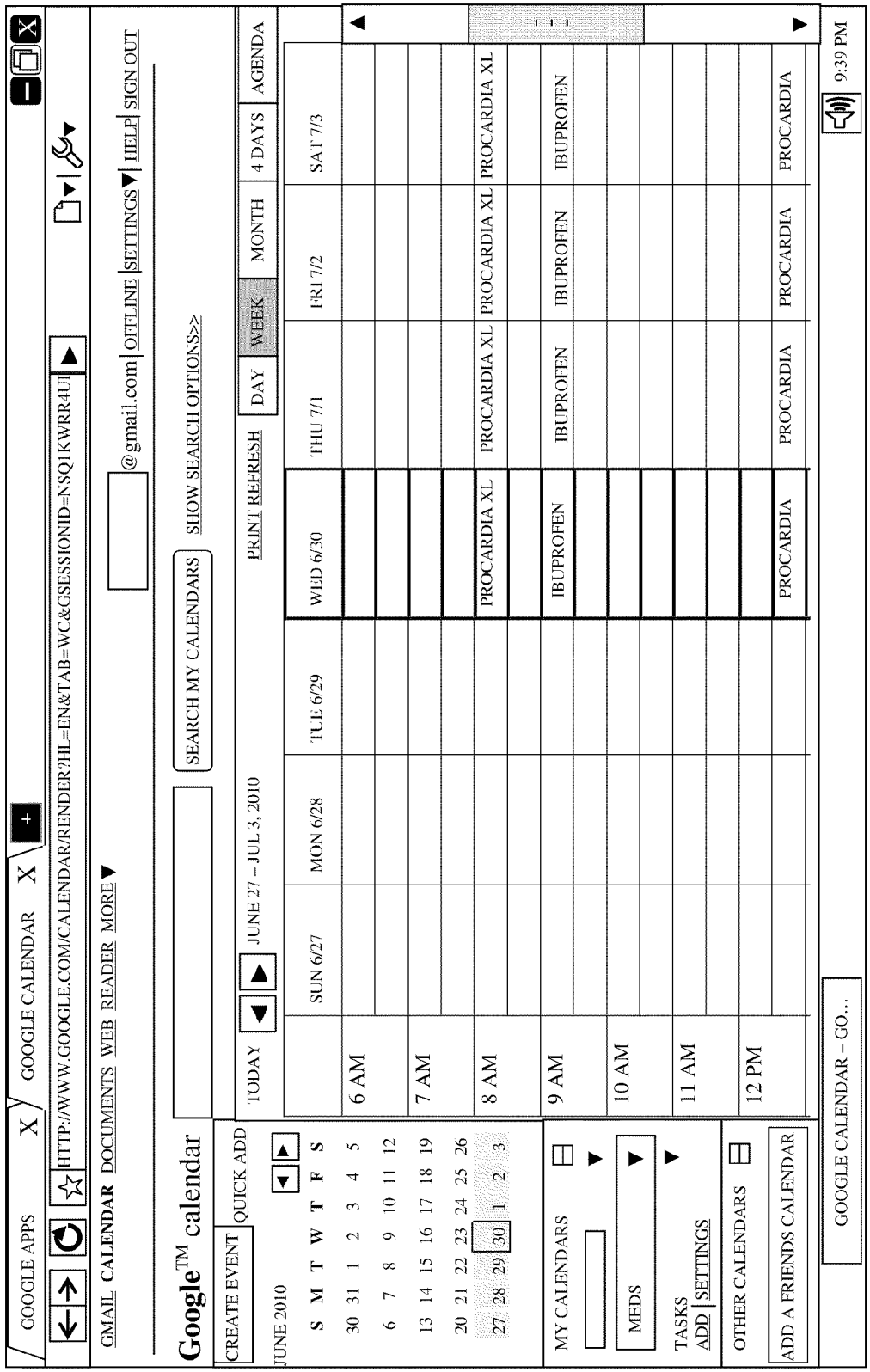
FIG. 8E exemplarily illustrates a screenshot of a sample resident daily medication schedule generated by the medication management application on the medication management platform.
Figure 8F:
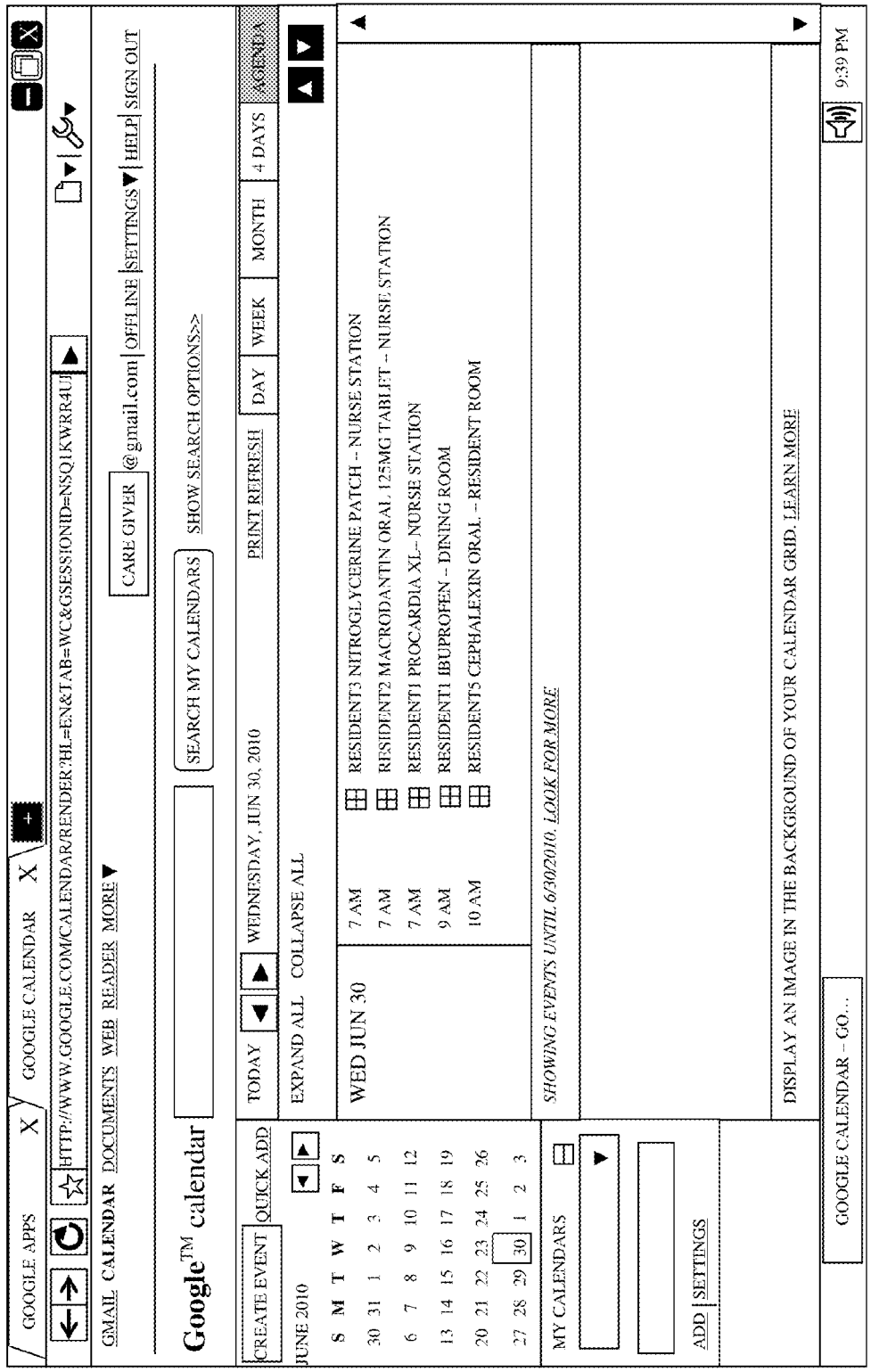
FIG. 8F exemplarily illustrates a screenshot of a sample daily task list generated by the medication management application on the medication management platform.
Figure 8G:
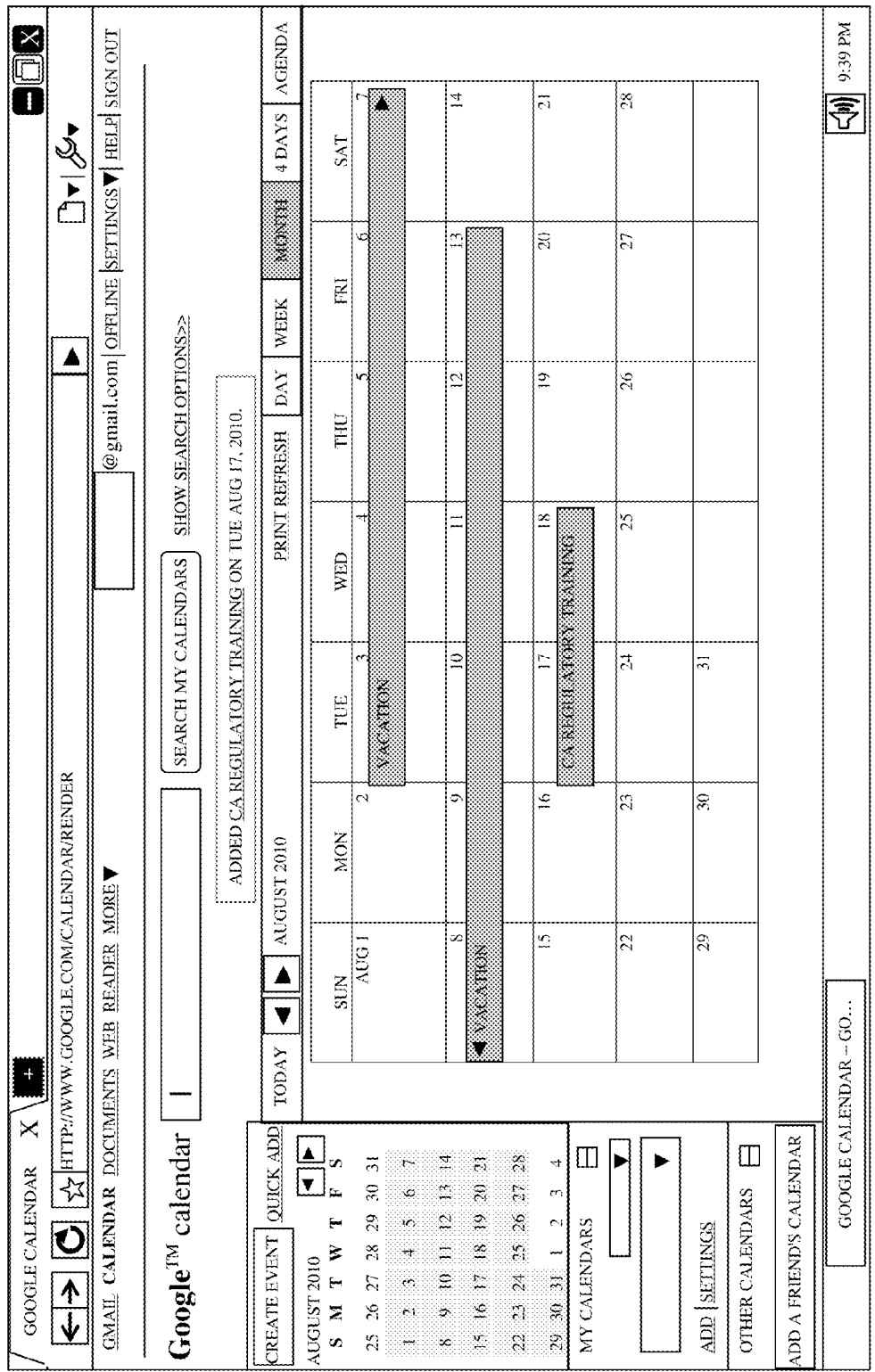
FIG. 8G exemplarily illustrates a screenshot of a monthly availability schedule of a health care provider generated by the medication management application on the medication management platform.

FIG. 8E exemplarily illustrates a screenshot of a sample resident daily medication schedule generated by the medication management application 201 on the medication management platform 200. The daily medication scheduler 201b generates the daily medication schedule for the resident based on the Google Calendar. The daily medication schedule is generated based on the administration instructions for the resident's prescriptions. The daily medication scheduler 201b makes the schedule available to the family of the resident as well. The daily task generator 201e generates a daily task list for the staff members such as the medical technicians of the assisted living facility (ALF) based on the recommendations from the schedule optimization engine 201f. FIG. 8F exemplarily illustrates a screenshot of a sample daily task list generated by the medication management application 201 on the medication management platform 200. FIG. 8G exemplarily illustrates a screenshot of a monthly availability schedule of a health care provider, for example, a medical technician.

Figure 8H:
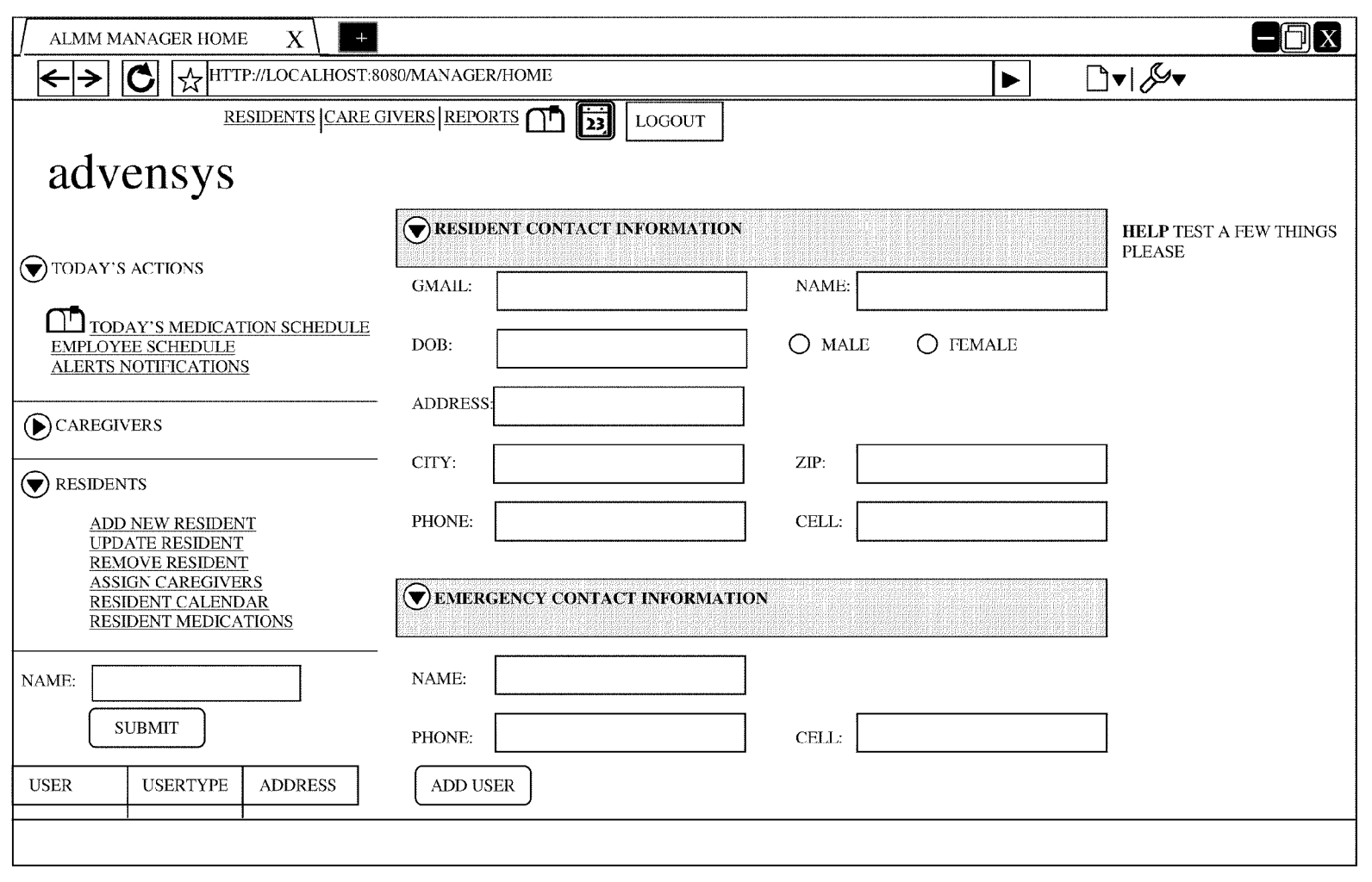
Figure 8I:
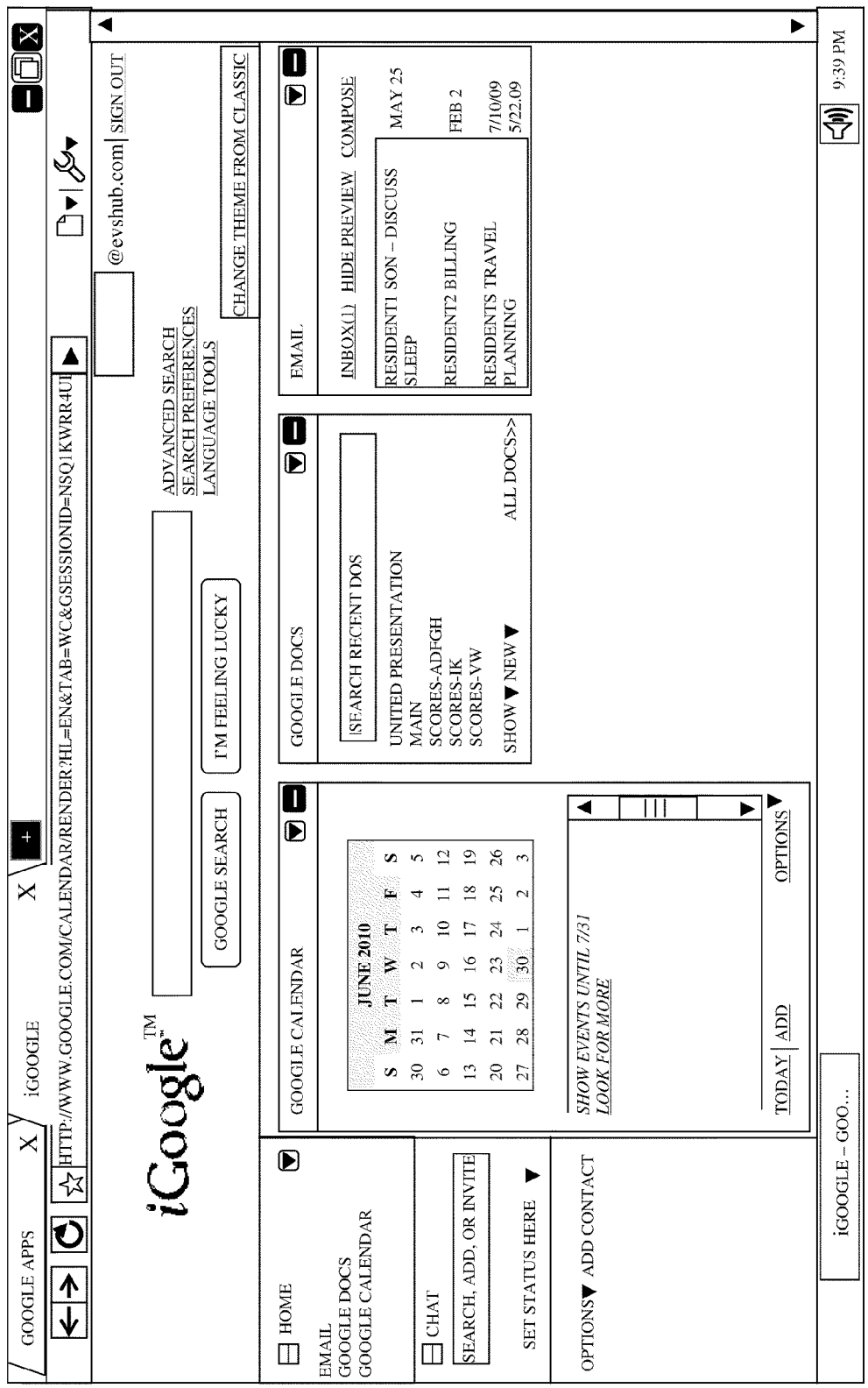
FIG. 8I exemplarily illustrates a screenshot of a sample assisted living facility collaboration web page.

FIG. 8H exemplarily illustrates a screenshot of sample resident registration web page for assisted living administration. The administrative functionality provided by the medication management platform 200 allows ALF managers to add residents, employees, staff members, etc. using the medication management application 201. The collaboration tools 203 enable employees to communicate among themselves and with the residents and their families and track efforts online. FIG. 8I exemplarily illustrates a screenshot of a sample assisted living collaboration web page. As exemplarily illustrated in FIG. 8I, collaboration is facilitated using hosted applications for electronic mail, chat, voice and video calls, micro blogging, and newer real-time collaboration tools. These and other features from Google Inc. are integrated on individual employee web start pages to allow quick and easy access to the collaboration tools 203.

Consider an example where a senior health care user signs up to become an assisted living facility (ALF) resident. An ALF administrator logs in to the medication management platform 200 using the login web page exemplarily illustrated in FIG. 8A. After logging in, the administrator enters information about the new resident and the resident's family as exemplarily illustrated in FIG. 8H, and information about the resident's Google PHR. Once the resident has been enrolled, the resident logs into the resident's Google account using the login web page as exemplarily illustrated in FIG. 8B. The resident also logs into the Google PHR as exemplarily illustrated in FIG. 8D to share the health care information with the medication management platform 200. The resident, the resident's family, or an enabled health care provider or ALF caregiver enters medication information in the Google PHR illustrated in FIG. 8D.

The health care provider sets up a resident daily medication schedule, as exemplarily illustrated in FIG. 8E, for example, on the Google Calendar. This resident daily medication schedule is shared across the facility calendar and optimized with the schedules for other residents and the independent health care provider schedules illustrated in FIG. 8G to create the facility master schedule. The facility master schedule is optimized for staff availability and resident medication needs to generate the individual health care provider or medical technician daily task lists. The health care provider or medical technician logs in to the medication management platform 200 on a daily basis to review their tasks and prepare medication carts to disburse medications, as exemplarily illustrated in FIG. 8F. Researchers may also log into the medication management platform 200 using the login web page illustrated in FIG. 8C to obtain analytical insights using the health care information in the research repository 202b. On a regular basis, the medical technicians, the residents, the family members and other health care providers log into their individual accounts to collaborate and share information using the assisted living collaboration page illustrated in FIG. 8I.

It will be readily apparent that the various methods and algorithms described herein may be implemented in a computer readable medium appropriately programmed for general purpose computers and computing devices. Typically a processor, for example, one or more microprocessors will receive instructions from a memory or like device, and execute those instructions, thereby performing one or more processes defined by those instructions. Further, programs that implement such methods and algorithms may be stored and transmitted using a variety of media, for example, computer readable media in a number of manners. In an embodiment, hard-wired circuitry or custom hardware may be used in place of, or in combination with, software instructions for implementation of the processes of various embodiments. Thus, embodiments are not limited to any specific combination of hardware and software. A "processor" means any one or more microprocessors, central processing unit (CPU) devices, computing devices, microcontrollers, digital signal processors or like devices. The term "computer readable medium" refers to any medium that participates in providing data, for example instructions that may be read by a computer, a processor or a like device. Such a medium may take many forms, including but not limited to, non-volatile media, volatile media, and transmission media. Non-volatile media include, for example, optical or magnetic disks and other persistent memory volatile media include dynamic random access memory (DRAM), which typically constitutes the main memory. Transmission media include coaxial cables, copper wire and fiber optics, including the wires that comprise a system bus coupled to the processor. Common forms of computer readable media include, for example, a floppy disk, a flexible disk, hard disk, magnetic tape, any other magnetic medium, a compact disc-read only memory (CD-ROM), digital versatile disc (DVD), any other optical medium, punch cards, paper tape, any other physical medium with patterns of holes, a random access memory (RAM), a programmable read only memory (PROM), an erasable programmable read only memory (EPROM), an electrically erasable programmable read only memory (EEPROM), a flash memory, any other memory chip or cartridge, a carrier wave as described hereinafter, or any other medium from which a computer can read. In general, the computer readable programs may be implemented in any programming language. Some examples of languages that can be used include C, C++, C#, Perl, Python, or JAVA. The software programs may be stored on or in one or more mediums as an object code. A computer program product comprising computer executable instructions embodied in a computer readable medium comprises computer parsable codes for the implementation of the processes of various embodiments.

Where databases are described such as the research repository 202b, it will be understood by one of ordinary skill in the art that (i) alternative database structures to those described may be readily employed, and (ii) other memory structures besides databases may be readily employed. Any illustrations or descriptions of any sample databases presented herein are illustrative arrangements for stored representations of information. Further, despite any depiction of the databases as tables, other formats including relational databases, object-based models and/or distributed databases could be used to store and manipulate the data types described herein. Likewise, object methods or behaviors of a database can be used to implement various processes, such as those described herein. In addition, the databases may, in a known manner, be stored locally or remotely from a device that accesses data in such a database.

The present invention can be configured to work in a network environment including a computer that is in communication, via a communications network, with one or more devices. The computer may communicate with the devices directly or indirectly, via a wired or wireless medium such as the Internet, a local area network (LAN), a wide area network (WAN) or the Ethernet, token ring, or via any appropriate communications means or combination of communications means. Each of the devices may comprise computers, such as those based on the Intel® processors, AMD® processors, UltraSPARC® processors, Sun® processors, IBM® processors, etc. that are adapted to communicate with the computer. Any number and type of machines may be in communication with the computer.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A computer implemented method for managing health care and obtaining analytical insights using information related to said health care in a collaborative environment, comprising:

providing a computer system comprising one or more processors, said processor configured to implement the following:

providing a medication management platform comprising a medication management application and a research repository, wherein said medication management platform is accessed by a plurality of health care users and health care providers in said collaborative environment, and wherein said research repository comprises a plurality of analytical data registries configured to obtain analytical insights that facilitate research on aging processes, age-related diseases and special needs of aged health care users, drug post-marketing surveillance, early detection of adverse drug events, study of prescription trends and usage, study of compliance of medication by said health care users, identification of off-label drug use, and enhanced information on actual drug ingestion;

providing a plurality of collaboration tools on said medication management platform to provide said health care users and said health care providers a platform to interact and communicate with each other in said collaborative environment;

providing a family collaborator tool on said medication management platform configured to track information of families of said health care users and for said families of said health care users to reach out to said health care providers and vice versa;

acquiring health care information of said health care users from a plurality of health care information sources using said collaboration tools;

acquiring online portable personal health records of said health care users as one of said health care information sources and integrating said online portable personal health records with said medication management application and acquiring specific health care information related to said health care users, wherein said medication management platform builds assisted living facilities management functions around said acquired online portable personal health records of said health care users and said health care providers;

monitoring and tracking said acquired health care information by said medication management application;

arranging a medical cart by reviewing said acquired health care information and stocking up medications on said medical cart by said medication management application;

updating said research repository by consolidating said monitored and tracked health care information and said medical cart information;

analyzing said consolidated health care information in said updated research repository and obtaining said analytical insights related to said health care, wherein said analytical insights are correlated with geography of said health care users to derive geo inferences.

2. The computer implemented method of claim 1, wherein said medication management platform is a cloud computing based platform implemented as a service configured to develop and host scalable web applications and services and manage said health care information.

3. The computer implemented method of claim 1, wherein said health care users and said health care providers are senior citizens, assisted living facilities, assisted living facility residents, nursing homes, pharmaceuticals, physicians, health care payers, and government organizations.

4. The computer implemented method of claim 1, wherein said research repository is a cloud computing based scalable research repository incorporating different levels of security and provides scalable access for researchers.

5. The computer implemented method of claim 1, further comprising providing an analytical visualization dashboard configured to render pre-built analytical insights and trends based on said consolidated health care information.

6. The computer implemented method of claim 1, further comprising providing application programming interfaces for querying and extracting data, policies, and metadata to facilitate research using said research repository.

7. The computer implemented method of claim 1, wherein said collaboration tools comprise hosted applications for electronic mail, chat, instant messaging, calendar, voice and video messaging, online sharing of documents and work optimization elements to facilitate collaboration between said health care users and said health care providers, assisted living facility medication managers, assisted living facility residents, resident families, pharmacies, and physicians.

8. The computer implemented method of claim 1, further comprising acquiring and storing prescription information and user information of said health care users across said health care providers subscribing to said medication management platform, wherein said prescription information and said user information is acquired from online portable personal health records of each of said health care users.

9. The computer implemented method of claim 1, further comprising generating a daily medication schedule for each of said health care users by said medication management application based on administration instructions of said health care providers for prescription schedules of each of said health care users.

10. The computer implemented method of claim 1, further comprising generating a facility master schedule for each of said health care providers and managing schedules of said health care users and staff members of each of said health care providers.

11. The computer implemented method of claim 10, further comprising tracking job schedules of each of said staff members of said health care providers and creating daily task lists for said each of said staff members by collating information from said job schedules and said facility master schedule.

12. The computer implemented method of claim 10, further comprising evaluating, on a daily basis, availability schedules of said staff members of each of said health care providers against medication administration needs for each day from said facility master schedule and creating daily task lists.

13. The computer implemented method of claim 1, further comprising generating reports for operational and regulatory management, wherein said reports ensure health insurance portability and accountability act compliance and compliance with state regulations, and facilitate managerial tracking.

14. A computer implemented system for managing health care and obtaining analytical insights using information related to said health care in a collaborative environment, comprising:
a computer system comprising one or more processors, said computer system comprising:
a medication management platform accessed by a plurality of health care users and health care providers in said collaborative environment, said medication management platform comprising:
a plurality of collaboration tools that acquires health care information of said health care users from a plurality of health care information sources, wherein said collaboration tools enables said health care users and said health care providers to interact and communicate with each other in said collaborative environment, and wherein one of said health care information sources comprises online portable personal health records that are integrated with said medication management application for acquiring specific health care information related to said health care users, and
wherein said medication management platform builds assisted living facilities management functions around said acquired online portable personal health records of said health care users and said health care providers;
providing a family collaborator tool configured to track information of families of said health care users and for said families of said health care users to reach out to said health care providers and vice versa;
a medication management application performing:
monitoring and tracking said acquired health care information; and
arranging a medical cart by reviewing said acquired health care information and stocking up medications on said medical cart; and
a research repository component comprising:
a research repository that consolidates said monitored and tracked health care information and said medical cart information, wherein said research repository comprises a plurality of analytical data registries configured to obtain analytical insights that facilitate research on aging processes, age-related diseases and special needs of aged health care users, drug post-marketing surveillance, early detection of adverse drug events, study of prescription trends and usage, study of compliance of medication by said health care users, identification of off-label drug use, and enhanced information on actual drug ingestion;
an analytical processor that analyzes said consolidated health care information in said research repository and obtains said analytical insights related to said health care, wherein said analytical insights are correlated with geography of said health care users to derive geo inferences.

15. The computer implemented system of claim 14, wherein said medication management platform is a cloud computing based platform implemented as a service configured to develop and host scalable web applications and services and manage said health care information.

16. The computer implemented system of claim 14, wherein said research repository is a cloud computing based scalable research repository incorporating different levels of security and provides scalable access for researches, and wherein said de-identification of said consolidated health care information safeguards privacy of said health care users.

17. The computer implemented system of claim 14, wherein said analytical processor provides an analytical visualization dashboard that renders pre-built analytical insights and trends based on said consolidated health care information.

18. The computer implemented system of claim 14, wherein said research repository component further comprises application programming interfaces for querying and extracting data, policies, and metadata to facilitate research using said research repository.

19. The computer implemented system of claim 14, wherein said collaboration tools comprise hosted applications for electronic mail, chat, instant messaging, calendar, voice and video messaging, online sharing of documents and work optimization elements to facilitate collaboration between said health care users and said health care providers, assisted living facility medication managers, assisted living facility residents, resident families, pharmacies, and physicians.

20. The computer implemented system of claim 14, wherein said medication management application comprises a prescriptions module that acquires and stores prescription information and user information of said health care users across said health care providers subscribing to said medication management platform, wherein said prescription information and said user information is acquired from online portable personal health records of each of said health care users.

21. The computer implemented system of claim 14, wherein said medication management application comprises a daily medication scheduler that generates a daily medication schedule for each of said health care users based on administration instructions of said health care providers for prescription schedules of each of said health care users.

22. The computer implemented system of claim 14, wherein said medication management application comprises a facility master scheduler that generates a facility master schedule for each of said health care providers and manages schedules of said health care users and staff members of each of said health care providers.

23. The computer implemented system of claim 22, wherein said medication management application further comprises a staff scheduler that tracks job schedules of each of said staff members of said health care providers and creates daily task lists for said each of said staff members by collating information from said job schedules and said facility master schedule.

24. The computer implemented system of claim 22, wherein said medication management application further comprises a schedule optimization engine that evaluates, on a daily basis, availability schedules of said staff members of each of said health care providers against medication administration needs for each day from said facility master schedule and creates daily task lists, and wherein said medication management application further comprises a daily task generator that generates said daily task lists for said staff members of each of said health care providers based on recommendations from said schedule optimization engine.

25. The computer implemented system of claim 14, wherein said medication management application comprises a reporting module that generates reports for operational and regulatory management, wherein said reports ensure health insurance portability and accountability act compliance and compliance with state regulations, and facilitate managerial tracking.

26. A computer program product comprising computer executable instructions embodied in a non-transitory computer system readable storage medium, wherein when executed by said computer, said computer program product presents the following:
a first computer parsable program code configured to provide a medication management platform comprising a medication management application and a research repository, wherein said medication management platform is accessible by a plurality of health care users and health care providers in a collaborative environment;
a second computer parsable program code configured to provide a plurality of collaboration tools on said medication management platform for enabling said health care users and said health care providers to interact and communicate with each other in said collaborative environment, wherein said research repository comprises a plurality of analytical data registries configured to obtain analytical insights that facilitate research on aging processes, age-related diseases and special needs of aged health care users, drug post-marketing surveillance, early detection of adverse drug events, study of prescription trends and usage, study of compliance of medication by said health care users, identification of off-label drug use, and enhanced information on actual drug ingestion;
a third computer parsable program code configured to acquire health care information of said health care users from a plurality of health care information sources using said collaboration tools;
a fourth computer parsable program code configured to provide a family collaborator tool on said medication management platform for tracking information of families of said health care users and for said families of said health care users to reach out to said health care providers and vice versa;
a fifth computer parsable program code configured to acquire online portable personal health records of said health care users as one of said health care information sources and integrating said online portable personal health records with said medication management application for acquiring specific health care information related to said health care users, wherein said medication management platform builds assisted living facilities management functions around said acquired online portable personal health records of said health care users and said health care providers;
a sixth computer parsable program code configured to monitor and track said acquired health care information by said medication management application;
a seventh computer parsable program code configured to arrange a medical cart by reviewing said acquired health care information and stocking up medications on said medical cart;
an eighth computer parsable program code configured to update said research repository by consolidating said monitored and tracked health care information and said medical cart information;
a ninth computer parsable program code configured to analyze said consolidated health care information in said updated research repository for obtaining said analytical insights related to said health care, wherein said analytical insights are correlated with geography of said health care users to derive geo inferences.

* * * * *